(12) United States Patent
Hu et al.

(10) Patent No.: US 11,345,754 B2
(45) Date of Patent: May 31, 2022

(54) MONOCLONAL ANTIBODY ANTAGONIZING AND INHIBITING THE BINDING OF HUMAN PD-1 ANTIGEN TO ITS LIGAND, PREPARATION METHOD THEREFOR AND APPLICATION THEREOF

(71) Applicant: Acroimmune Biotech Co., Ltd., Guangzhou (CN)

(72) Inventors: Hongqun Hu, Suzhou (CN); Zui Chen, Suzhou (CN); Xiaoqi Song, Suzhou (CN); Shiping Luo, Suzhou (CN); Mingwen Cai, Suzhou (CN); Jinling Fan, Suzhou (CN); Yiqing Xu, Suzhou (CN); Qunmin Zhou, Suzhou (CN)

(73) Assignee: AcroImmune Biopharma Co., Ltd., Nanjing (CN)

( * ) Notice: Subject to any disclaimer, the term of this patent is extended or adjusted under 35 U.S.C. 154(b) by 413 days.

(21) Appl. No.: 16/606,779

(22) PCT Filed: Jun. 21, 2017

(86) PCT No.: PCT/CN2017/089282
§ 371 (c)(1),
(2) Date: May 9, 2020

(87) PCT Pub. No.: WO2018/192089
PCT Pub. Date: Oct. 25, 2018

(65) Prior Publication Data
US 2020/0277376 A1 Sep. 3, 2020

(30) Foreign Application Priority Data
Apr. 20, 2017 (CN) .......................... 201710262053.4

(51) Int. Cl.
| C07K 16/28 | (2006.01) |
| A61K 39/395 | (2006.01) |
| A61P 35/00 | (2006.01) |
| C07K 1/22 | (2006.01) |
| A61K 39/00 | (2006.01) |

(52) U.S. Cl.
CPC .......... *C07K 16/2818* (2013.01); *A61P 35/00* (2018.01); *C07K 1/22* (2013.01); *A61K 2039/505* (2013.01); *C07K 2317/24* (2013.01); *C07K 2317/522* (2013.01); *C07K 2317/524* (2013.01); *C07K 2317/526* (2013.01); *C07K 2317/565* (2013.01)

(58) Field of Classification Search
None
See application file for complete search history.

(56) References Cited

U.S. PATENT DOCUMENTS

| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,354,509 | B2 | 1/2013 | Carven et al. |
| 9,815,897 | B2 * | 11/2017 | King .................. C07K 16/2818 |
| 2009/0217401 | A1 | 8/2009 | Korman et al. |
| 2010/0266617 | A1 | 10/2010 | Carven et al. |

FOREIGN PATENT DOCUMENTS

| CN | 101213297 A | 7/2008 |
| CN | 101248089 A | 8/2008 |
| CN | 101899114 A | 12/2010 |
| CN | 102892786 A | 1/2013 |
| CN | 104250302 A | 12/2014 |
| CN | 103242448 B | 1/2015 |
| CN | 104558177 A | 4/2015 |
| CN | 104560884 A | 4/2015 |
| CN | 103059138 B | 10/2015 |
| CN | 105026428 A | 11/2015 |
| CN | 105061597 A | 11/2015 |
| CN | 105431059 A | 3/2016 |
| CN | 105531288 A | 4/2016 |
| CN | 107090041 A | 8/2017 |
| EP | 3026062 A1 | 6/2016 |
| WO | 2008156712 A1 | 12/2008 |
| WO | 2014179664 A2 | 11/2014 |
| WO | WO 2014/179664 | * 11/2014 |

OTHER PUBLICATIONS

Yasumasa Ishida, Yasutoshi Agata, Keiichi Shibahara and Tasuku Honjo, Induced expression of PD-1, a novel member of the immunoglobulin gene superfamily, upon programmed cell death, The EMBO Journal, 1992, pp. 3887-3895, vol. 1 1 No. 11.

Changyu Wang, Kent B. Thudium, Minhua Han, et al., In Vitro Characterization of the Anti-PD-1 Antibody Nivolumab, BMS-936558, and In Vivo Toxicology in Non-Human Primates, Cancer Immunol Res Published OnlineFirst, May 28, 2014, p. 1-11, 2.

Ganesh Suntharalingam, et al. Cytokine Storm in a Phase 1 Trial of the Anti-CD28 Monoclonal Antibody TGN1412, The New England Journal of Medicine, Aug. 14, 2006, p. 1018-28, 355.

J. Naidoo et al., Toxicities of the anti-PD-1 and anti-PD-L1 immune checkpoint antibodies, Annals of Oncology, 2015, p. 2375-2391, 26.

Mary E. Keir, Manish J. Butte,Gordon J. Freeman, and Arlene H. Sharpe, PD-1 and Its Ligands in Tolerance and Immunity, Annu. Rev. Immunol. 2008, p. 677-704, 26.

(Continued)

*Primary Examiner* — Laura B Goddard
(74) *Attorney, Agent, or Firm* — Bayramoglu Law Offices LLC

(57) ABSTRACT

A monoclonal antibody or a derivative thereof which can antagonize and inhibit the binding of human PD-1 antigen to its ligand: the amino acid sequences of CDR1, CDR 2 and CDR 3 in the light chain variable region of the antibody are shown in SEQ ID NO:3, SEQ ID NO: 4 and SEQ ID NO: 5, respectively, while the amino acid sequences of CDR 1, CDR 2 and CDR 3 in the heavy chain variable region are shown in SEQ ID NO: 8, SEQ ID NO: 9 and SEQ ID NO: 10, respectively. A humanization preparation process for the antibody and the amino acid sequences of the heavy chain variable region and light chain variable region of the humanized antibody.

15 Claims, 12 Drawing Sheets

Specification includes a Sequence Listing.

(56) References Cited

OTHER PUBLICATIONS

David B. Page, Michael A. Postow, Margaret K. Callahan, James p. Allison, and Jedd D. Wolchok, Immune Modulation in Cancer with Antibodies, Annu. Rev. Med. 2014, p. 185-202, 65.

Takeshi Azuma et al., B7-H1 is a ubiquitous antiapoptotic receptor on cancer cells, Blood, Apr. 1, 2008, vol. 111, No. 7.

Ying Wang et al., Degenerated primer design to amplify the heavy chain variable region from immunoglobulin Cdna, BMC Bioinformatics, 2006, p. 9, 7 Suppl, 4.

S A Quezada et al., Exploiting CTLA-4, PD-1 and PD-L1 to reactivate the host immune response against cancer, British Journal of Cancer 2013, p. 1560-1565, 108.

Hiroyuki Nishimura et al., Autoimmune Dilated Cardiomyopathy in PD-1 Receptor-Deficient Mice, Science, Jan. 12, 2001, vol. 291: 319.

Suzanne L. Topalian et al., Safety, Activity, and Immune Correlates of Anti-PD-1 Antibody in Cancer, The New England Journal of Medicine, Jun. 28, 2443-2454, 2012 vol. 366 No. 26.

Peter J.K. Van Meer et al., Immunogenicity of mAbs in non-human primates during nonclinical safety assessment, Landes Bioscience, 2013, p. 810-816, vol. 5 No. 5.

Fumiya Hirano et al., Blockade of B7-H1 and PD-1 by Monoclonal Antibodies Potentiates Cancer Therapeutic Immunity, Cancer Res 2005, p. 1089-1096, 65: 3.

R. Houston Thompson et al., Tumor B7-H1 Is Associated with Poor Prognosis in Renal Cell Carcinoma Patients with Long-term Follow-up, Cancer Res 2006; 66, 7.

Hiroyuki Nishimura et al., Development of Lupus-like Autoimmune Diseases by Disruption of the PD-1 Gene Encoding an ITIM Motif-Carrying Immunoreceptor, Cell Press, Immunity, Aug. 1999, vol. 11, 141-151.

Soo-Jeet Teh et al., Fas (CD95)-independent regulation of immune responses by antigen-specific CD4"CD8+ T cells, International Immunology, 1996, pp. 675-681, vol. 8, No. 5.

Julie R. Brahmer et al. Phase I Study of Single-Agent Anti-Programmed Death-1 (MDX-1106) in Refractory Solid Tumors: Safety, Clinical Activity, Pharmacodynamics, and Immunologic Correlates, Journal Of Clinical Oncology, Jul. 1, 2010, p. 3167-75, vol. 28 No 19.

Suzanne L. Topalian et al., Cancer Immunotherapy Comes of Age, Journal of Clinical Oncology, Dec. 2011, vol. 29 No 36.

Gordon J. Freeman et al., Engagement of the PD-1 Immunoinhibitory Receptor by a Novel B7 Family Member Leads to Negative Regulation of Lymphocyte Activation, J. Exp. Med., Oct. 2, 2000, p. 1027-1034, The Rockefeller University Press, vol. 192, No. 7.

Su-Yi Tseng et al., B7-DC, a New Dendritic Cell Molecule with Potent Costimulatory Properties for T Cells, J. Exp. Med., Apr. 2, 2001, p. 839-845, The Rockefeller University Press, No. 7—vol. 193.

Mary E. Keir et al., Tissue expression of PD-L1 mediates peripheral T cell tolerance, The Journal of Experimental Medicine, Apr. 17, 2006, vol. 203.

Drew Pardoll et al., Immunotherapy earns its spot in the ranks of cancer therapy, The Journal of Experimental Medicine, vol. 209, No. 2.

Caroline Robert, Anti-programmed-death-receptor-1 treatment with pembrolizumab in ipilimumab-refractory advanced melanoma: a randomised dose-comparison cohort of a phase 1 trial, Lancet, 2014, p. 1109-17, 384.

Drew M. Pardoll, The blockade of immune checkpoints in cancer immunotherapy, Nature, Apr. 2012, vol. 12.

Julie R. Brahmer et al., Safety and Activity of Anti-PD-L1 Antibody in Patients with Advanced Cancer, The New England Journal of Medicine, 2012, p. 2455-65, 366.

Omid Hamid et al., Safety and Tumor Responses with Lambrolizumab (Anti-PD-1) in Melanoma, The New England Journal of Medicine, 2013, p. 134-44, 369.

Caroline Robert et al., Nivolumab in Previously Untreated Melanoma without BRAF Mutation, The New England Journal of Medicine, 2015, p. 320-30, 372.

Yvette Latchman et al., PD-L2 is a second ligand for PD-1 and inhibits T cell activation, Nature Publishing Group, Mar. 2001, vol. 2 No. 3.

Haidong Dong et al., B7-H1, a third member of the B7 family, co-stimulates T-cell proliferation and interleukin-10 secretion, Nature Medicine, Dec. 1999, p. 1365-1369, vol. 5, No. 12.

Haidong Dong et al., Tumor-associated B7-H1 promotes T-cell apoptosis: A potential mechanism of immune evasion. Nature Medicine, Aug. 2002, vol. 8, No. 8.

Alexandra Flemming, PD1 makes waves in anticancer immunotherapy, Research Highlight, Aug. 2012, Nature Reviews, Drug Discovery, vol. 11.

Lieping Chen, Co-Inhibitory Molecules Of The B7-Cd28 Family In The Control Of T-Cell Immunity, May 2004, vol. 4, Nature Publishing Group.

G. Kohler, C. Milstein, Continuous cultures of fused cells secreting antibody of predefined specificity, Nature, Aug. 7, 1975, vol. 256.

Hugues Lortat-Jacob et al., Structural diversity of heparan sulfate binding domains in chemokines, PNAS, Feb. 5, 2002, p. 1229-1234, vol. 99 , No. 3.

* cited by examiner

Alignment of human and mouse PD-1: Identities: 172/288 (60%)

```
                  Signal peptide                              IgV domain (35-144)
hPD1    1    MQIPQAPWPVVWAVLQLGWRPGWFLDSPDRPWNPPTFSPALLVVTEGDNATFTCSFSNTS   60
             M + Q PW   WAVLQL W+ GW L+ P+ PW    TF PA L V+EG NATFTCS SN S
mPD1    1    MWVRQVPWSFTWAVLQLSWQSGWLLEVPNGPWRSLTFYPAWLTVSEGANATFTCSLSNWS   60 hPD1   61    ESFVLNWYRMSPSNQTDKLAAFPEDRSQPGQDCRFRVTQLPNGRDFHMSVVRARRNDSGT  120
             E  +LNW R+SPSNQT+K AAF   SQP QD RF++ QLPN  DFHM+++ R NDSG
mPD1   61    EDLMLNWNRLSPSNQTEKQAAFCNGLSQPVQDARFQIIQLPNRHDFHMNILDTRRNDSGI  120

TM region
hPD1  121    YLCGAISLAPKAQIKESLRAELRVTERRAEVPTAHPSPSPRPAGQFQTLVVGVVGGLLGS  180
             YLCGAISL PKA+I+ES  AEL VTER   E  T +PSPSP+P G+FQ  +V+G++ L+G
mPD1  121    YLCGAISLHPKAKIEESPGAELVVTERILETSTRYPSPSPKPEGRFQGMVIGIMSALVGI  180 hPD1  181    LV--LLVWVLAVICSRAARGTIGARRTGQPLKEDPSAVPVFSVDYGELDFQWREKTPEPP  238
               V  LL W LAV CS +    GA       LKE+PSA PV SV Y ELDFQ REKTPE P
mPD1  181    PVLLLLAWALAVFCSTSMSEARGAGSKDDTLKEEPSAAPVPSVAYEELDFQGREKTPELP  240 hPD1  239    VPCVPEQTEYATIVFPSGMGTSSPARRGSADGPRSAQPLRPEDGHCSWPL  288
             CV   TEYATIVF  G+G S+   RRGSADG +  +P R EDGH CSWPL
mPD1  241    TACV--HTEYATIVFTEGLGASAMGRRGSADGLQGPRPPRHEDGHCSWPL  288
```

Figure 1

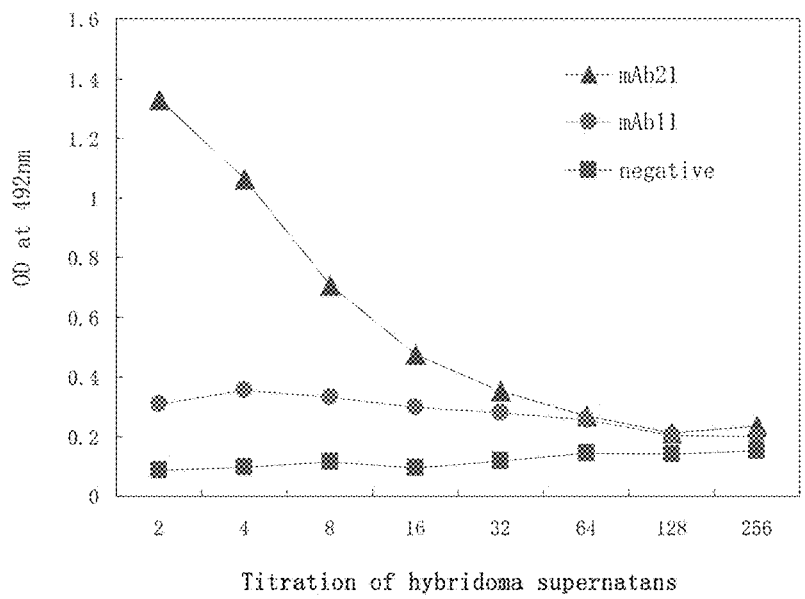

Figure 2

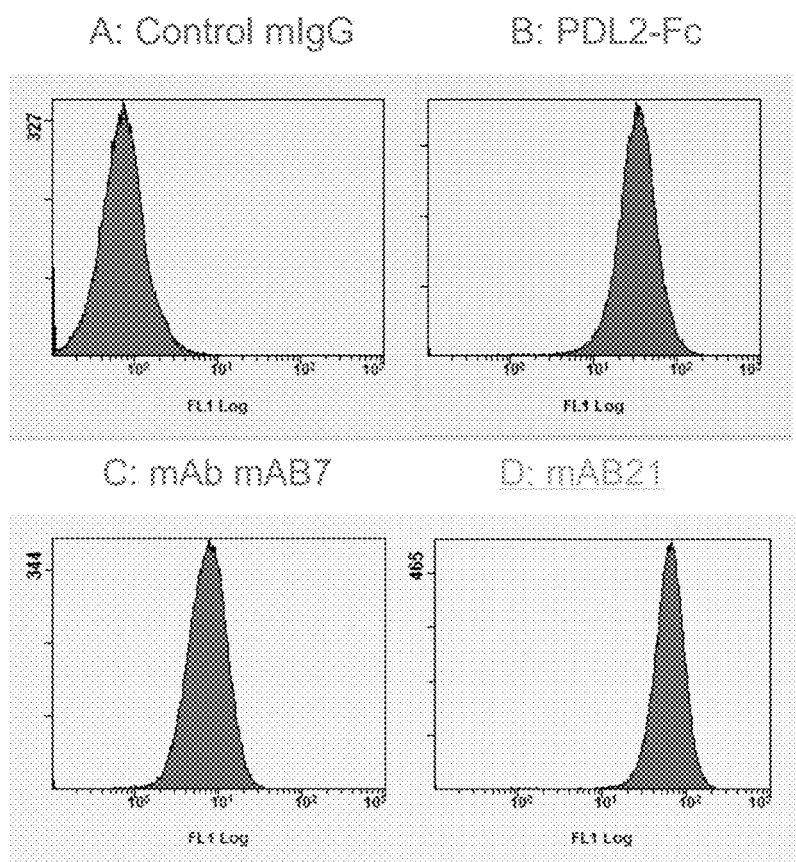
Figure 3
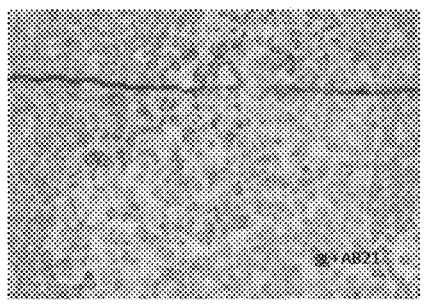
A. IHC staining of monkey spleen section with mAB21
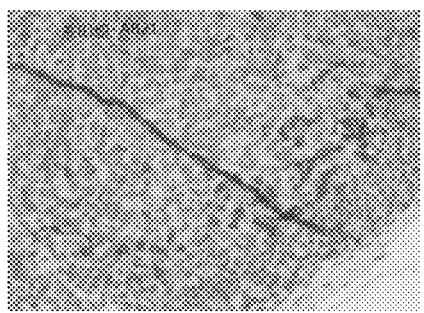
B. IHC staining of monkey lymph node with mAB21
Figure 4

```
                              CDR1                              CDR2
Nivo-L   1    EIVLTQSPATLSLSPGERATLSC RASQSVS----SYLA WYQQKPGQAPRLLIY DASNRAT   56
Ab21-L   1    XIVXTQSXXXSXSXGXRXXXXC  KASQXXXS   XXA  WYQQKPGXPLLIY  KASXRXT   56
MK3475L  1    EIVLTQSPATLSLSPGERATLSC RASKGVSTSGYSYLH WYQQKPGQAPRLLIY LASYLES   60

CDR3
Nivo-L   GIPARFSGSGSGTDFTLTISSLEPEDFAVYYCQQS SNWPRTFGQ GTKVEIK  107
Ab21-L   GXPXRFXGSGSGTDFTLTISXXXXXEXXXYFCQQX SXXPXTFGX GTKXEIK  107
MK3475L  GVPARFSGSGSGTDFTLTISSLEPEDFAVYYCQHS RDLPLTFGG GTKVEIK  111
```

Alignment of hAb21L, MK3475L and Nivolumab-light chain-V domain hAb21-L and Nivolumab-L    identities: 66/107 (62%)
hAb21-L and MK3475-L       identities: 61/111 (55%)
MK3475-L and Nivolumab-L   identities: 92/111 (83%)

Figure 6A

```
                              CDR1                              CDR2
Nivo-H   1    QVQLVESGGGVVQPGRSLRLDCKAS GITFSNSG MHWVRQAPGKGLEWVAV IWYDGSKRYY   60
hAb21-H  1    XVQLVESGGGLVQPGXSLRLSCXAS GXTFSXXX MSWVRQAPGKGLEWVXX IXXXGXXXYY   60
M3475-H  1    QVQLVQSGVEVKKPGASVKVSCKAS GYTFTNYY MYWVRQAPGQGLEWMGG INPSNGGTNF   60

CDR3
Nivo-H   ADSVKGRFTISRDNSKNTLFLQMNSLRAEDTAVYYCAT -------NDDY WGQGTLVTVSS  113
hAb21-H  XDSVKGRFTISRDNSKNTLXLQMNSLRAEDTAVYYCXX XXXXXXX DY  WGQGTXVTVSS  118
M3475-H  NEKFKNRVTLTTDSSTTAYMELKSLQFDDTAVYYCAR  RDYRFDMGFDY WGQGTTVTVSS  120
```

Alignment of hAb21H, MK3475-H and Nivolumab-heavy chain-V domain hAb21-H and Nivolumab-H    identities: 88/118 (75%)
hAb21-H and MK3475-H       identities: 60/120 (50%)
MK3475-H and Nivolumab-H   identities: 60/120 (50%)

Figure 6B

SEQUENCE LISTING

<160> NUMBER OF SEQ ID NOS: 20

<210> SEQ ID NO 1
<211> LENGTH: 321
<212> TYPE: DNA

<213> ORGANISM: Mus musculus

<400> SEQUENCE: 1

```
gacattgtga tgacccagtc tcacaaattc atgtccacat cagtgggaga cagggtcagc    60
atcacctgca aggccagtca ggatgcgggt tctgctgtag cctggtatca acagaaacca   120
ggacaatctc ctaaactact gatttactgg gcatccactc ggcacactgg agtccctggt   180
cgcttcacag gcagtggatc tgggacagac ttcactctca ccattagcaa tgtgcagtct   240
gaagacttgt cagattattt ctgtcagcaa tatagcagct atccgtggac gttcggtgga   300
ggcaccaagc tggaaatcaa g                                              321
```

<210> SEQ ID NO 2
<211> LENGTH: 107
<212> TYPE: PRT
<213> ORGANISM: Mus musculus

<400> SEQUENCE: 2

```
Asp Ile Val Met Thr Gln Ser His Lys Phe Met Ser Thr Ser Val Gly
1               5                   10                  15
Asp Arg Val Ser Ile Thr Cys Lys Ala Ser Gln Asp Ala Gly Ser Ala
            20                  25                  30
Val Ala Trp Tyr Gln Gln Lys Pro Gly Gln Ser Pro Lys Leu Leu Ile
        35                  40                  45
Tyr Trp Ala Ser Thr Arg His Thr Gly Val Pro Gly Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ser Asp Tyr Phe Cys Gln Gln Tyr Ser Ser Tyr Pro Trp
                85                  90                  95
Thr Phe Gly Gly Gly Thr Lys Leu Glu Ile Lys
            100                 105
```

<210> SEQ ID NO 3
<211> LENGTH: 11
<212> TYPE: PRT
<213> ORGANISM: Homo sapiens

<400> SEQUENCE: 3

```
Lys Ala Ser Gln Asp Ala Gly Ser Ala Val Ala
1               5                   10
```

<210> SEQ ID NO 4
<211> LENGTH: 7
<212> TYPE: PRT
<213> ORGANISM: Homo sapiens

<400> SEQUENCE: 4

```
Trp Ala Ser Thr Arg His Thr
1               5
```

<210> SEQ ID NO 5
<211> LENGTH: 9
<212> TYPE: PRT
<213> ORGANISM: Homo sapiens

<400> SEQUENCE: 5

```
Ser Ser Tyr Pro Trp Thr Phe Gly Gly
1               5
```

```
<210> SEQ ID NO 6
<211> LENGTH: 357
<212> TYPE: DNA
<213> ORGANISM: Mus musculus

<400> SEQUENCE: 6
gaggtgcagc tggtggagtc tgggggagac tttgtgaagc ctggagggtc cctgaaactc      60
tcctgtgcag cctctggatt cactttcagt aggtatgata tgtcttgggt tcgccagact     120
ccagacaaga ggctggagtg ggtcgcaacc attagtggtg gtggtcgtta cacctactat     180
ccagacagtg tgaaggggcg attcaccatc tccagagaca atgccaagaa caccctgtac     240
ctgcaaatga gcagtctgaa gtctgaggac acagccattt atttctgtac aagtccctat     300
ggtaactacg gaatggacta ctggggtcaa ggaacctcag tcaccgtctc ctcagcc        357

<210> SEQ ID NO 7
<211> LENGTH: 119
<212> TYPE: PRT
<213> ORGANISM: Mus musculus

<400> SEQUENCE: 7

Glu Val Gln Leu Val Glu Ser Gly Gly Asp Phe Val Lys Pro Gly Gly
1               5                   10                  15

Ser Leu Lys Leu Ser Cys Ala Ala Ser Gly Phe Thr Phe Ser Arg Tyr
                20                  25                  30

Asp Met Ser Trp Val Arg Gln Thr Pro Asp Lys Arg Leu Glu Trp Val
            35                  40                  45

Ala Thr Ile Ser Gly Gly Gly Arg Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Phe Cys
                85                  90                  95

Thr Ser Pro Tyr Gly Asn Tyr Gly Met Asp Tyr Trp Gly Gln Gly Thr
            100                 105                 110

Ser Val Thr Val Ser Ser Ala
        115

<210> SEQ ID NO 8
<211> LENGTH: 8
<212> TYPE: PRT
<213> ORGANISM: Homo sapiens

<400> SEQUENCE: 8

Gly Phe Thr Phe Ser Arg Tyr Asp
1               5

<210> SEQ ID NO 9
<211> LENGTH: 10
<212> TYPE: PRT
<213> ORGANISM: Homo sapiens

<400> SEQUENCE: 9

Ile Ser Gly Gly Gly Arg Tyr Thr Tyr Tyr
1               5                   10

<210> SEQ ID NO 10
<211> LENGTH: 9
<212> TYPE: PRT
<213> ORGANISM: Homo sapiens
```

```
<400> SEQUENCE: 10

Pro Tyr Gly Asn Tyr Gly Met Asp Tyr
1               5

<210> SEQ ID NO 11
<211> LENGTH: 107
<212> TYPE: PRT
<213> ORGANISM: Artificial Sequence
<220> FEATURE:
<223> OTHER INFORMATION: the sequence is synthetized.

<400> SEQUENCE: 11

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Ala Gly Ser Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Trp
                85                  90                  95

Thr Phe Gly Gly Gly Thr Lys Leu Glu Ile Lys
            100                 105

<210> SEQ ID NO 12
<211> LENGTH: 119
<212> TYPE: PRT
<213> ORGANISM: Artificial Sequence
<220> FEATURE:
<223> OTHER INFORMATION: the sequence is synthetized.

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Arg Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ser Pro Tyr Gly Asn Tyr Gly Met Asp Tyr Trp Gly Gln Gly Thr
            100                 105                 110

Ser Val Thr Val Ser Ser Ala
        115

<210> SEQ ID NO 13
<211> LENGTH: 321
<212> TYPE: DNA
<213> ORGANISM: Artificial Sequence
<220> FEATURE:
<223> OTHER INFORMATION: the sequence is synthetized.

<400> SEQUENCE: 13
```

```
gacatccagc tgacccagtc ccccagcttc tgtccgctt ccgtgggcga cagggtgacc      60
atcacctgca aggcctccca ggatgccgga tccgctgtgg cctggtacca gcagaagccc     120
ggcaaggccc ctaagctgct gatctactgg gcttccacca ggcacaccgg cgtgccttcc     180
aggttttccg gctccggctc cggcacagag ttcaccctga ccatctcctc cctgcagccc     240
gaggacttcg ccacctacta ctgccagcag tacagctcct acccttggac cttcggcggc     300
ggcaccaagc tggagatcaa g                                                321
```

<210> SEQ ID NO 14
<211> LENGTH: 357
<212> TYPE: DNA
<213> ORGANISM: Artificial Sequence
<220> FEATURE:
<223> OTHER INFORMATION: the sequence is synthetized.

<400> SEQUENCE: 14

```
gaggtgcagc tggtggagtc cggcggagga ctggtgcaac tggcggaag cctgaggctg       60 tcctgtgccg cctccggctt caccttctcc aggtacgaca tgtcctgggt gaggcaggct     120
cctggcaagg gcctggagtg ggtgtccacc atttccggcg gcggcaggta cacctactac     180
cccgactccg tgaagggcag gttcaccatc tccagggaca actccaagaa caccctgtac     240
ctgcagatga actccctgag ggccgaggac accgccgtgt actactgcac cagcccctac     300
ggcaactacg gcatggacta ctggggccag ggcacctccg tgacagtgtc ctccgct        357
```

<210> SEQ ID NO 15
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 15

```
tgtcgttcac tgccatcaat                                                  20
```

<210> SEQ ID NO 16
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 16

```
gcaaggctta caaccacaat c                                                21
```

<210> SEQ ID NO 17
<211> LENGTH: 17
<212> TYPE: DNA
<213> ORGANISM: Artificial Sequence
<220> FEATURE:
<223> OTHER INFORMATION: The sequence is synthesized

<400> SEQUENCE: 17

```
gacattgtga tgwcmca                                                     17
```

<210> SEQ ID NO 18
<211> LENGTH: 20
<212> TYPE: DNA
<213> ORGANISM: Artificial Sequence
<220> FEATURE:
<223> OTHER INFORMATION: The sequence is synthesized

```
<400> SEQUENCE: 18
ctgaggcacc tccagatgtt                                                    20

<210> SEQ ID NO 19
<211> LENGTH: 17
<212> TYPE: DNA
<213> ORGANISM: Artificial Sequence
<220> FEATURE:
<223> OTHER INFORMATION: The sequence is synthesized

<400> SEQUENCE: 19
gtrcagcttc aggagtc                                                       17

<210> SEQ ID NO 20
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 20
gtgctggagg ggacagtcac t                                                  21
```

MONOCLONAL ANTIBODY ANTAGONIZING AND INHIBITING THE BINDING OF HUMAN PD-1 ANTIGEN TO ITS LIGAND, PREPARATION METHOD THEREFOR AND APPLICATION THEREOF

CROSS REFERENCE TO THE RELATED APPLICATIONS

This application is the national phase entry of International Application No. PCT/CN2017/089282, filed on Jun. 21, 2017, which is based upon and claims priority to Chinese Patent Application No. 201710262053.4, filed on Apr. 20, 2017, the entire contents of which are incorporated herein by reference.

TECHNICAL FIELD

The invention falls into the field of biotechnology—monoclonal antibody. The invention relates to a monoclonal antibody antagonizing and inhibiting binding of the programmed death receptor PD-1 (programmed death-1) to its ligand, the coding sequence thereof as well as the preparation and application thereof.

BACKGROUND

It has been long believed in the biomedical field that tumor formation and development is closely related to the function status of the host immune system. Normally, the host immune system plays a role of immune surveillance by surveilling the growth of mutated tumor cells and inhibiting tumor metastasis and reoccurrence. However, in case of the hypofunction or suppression of the host immune system, tumor metastasis and reoccurrence will accelerate and may be life-threatening in severe cases. Therefore, tumor immunotherapy, which attacks or kills tumor directly by mobilizing the host immunity, is one of the goals being pursued in clinic treatment of tumor. Since 2011, a string of major breakthrough in immunotherapy have revolutionized cancer treatment (Topalian S L et al: Cancer immunotherapy comes of age. JCO 2011; 29:4828-4836; Pardoll D & Drake C: Immunotherapy earns its spot in the ranks of cancer therapy. J Exp Med 2012; 209: 201-209; Page D B, Postow M A, Callahan M K, Allison J P and Wolchok J D: Immune modulation in cancer with antibodies. Annu Rev Med 2014; 65:185-202). These revolutionary breakthroughs mainly benefit from progress in basic immunological research as well as the advent and development of modern biotechnology represented by hybridoma, genetically engineered antibody, etc.

Basic immunological research shows that cellular immunity mediated by T lymphocytes (which develop from thymus) are extremely crucial in surveilling and/or directly attacking and killing off cancer cells. T lymphocyte can be broadly separated into two categories: T helper cells, which mainly regulate and control immune function, and cytotoxic T cells (CTL), which engage in recognizing target antigens and directly attack and kill target cells.

For the fully activation and proliferation of helper T cells or CTLs, it generally requires a synergy of two signal pathways. The signal 1 is antigen specific and is mediated by the interaction between T-cell receptor (TcR) expressed on T cells and antigen peptide-MHC (major histocompatibility complex) expressed on target cells or antigen-presenting cells (APC); the signal 2 is antigen non-specific and is mediated by the interaction between co-stimulatory molecules or co-inhibitory molecules expressed on T-cells and their corresponding ligands expressed on target cells or antigen presenting cells (APC).

Co-stimulatory molecules, which up-regulate immune response mainly include CD28 and its ligand B7-1 (CD80) or B7-2 (CD86), CD40 and its ligand CD40L, CD137 (also called 4-1BB) and its ligand CD137-L, and CD278 (ICOS, Inducible T-cell costimulatory) and its ligand ICOS-L.

Co-inhibitory molecules, which are also called immune checkpoint inhibitory, down-regulate immune response and mainly includes CTLA-4 (Cytotoxic T-lymphocyte Antigen-4) and its ligand B7-1 (CD80) or B7-2 (CD86), PD-1 (programmed death-1) and its ligand PD-L1 or PD-L2, LAG-3 (Lymphocyte activation gene-3) and its ligand, TIM-3 (T-cell Immunoglobulin domain and Mucin domain 3) and its ligand, BTLA (B and T Lymphocyte Attenuator) and its ligand.

These co-stimulatory/co-inhibitory molecules are very similar in-structure, and most of them are the members of immuneglobulin superfamily (Chen L P: Co-inhibitory molecules of the B7-CD28 family in the control of T cell immunity. Nature Immunol 2004, 336-347).

In principle, there are at least two different approaches to up-regulate immune response: approach 1 is to direct up-regulate T-cell function by increasing the expression or function of co-stimulatory molecules such as CD28 on T cells; approach 2 is to indirect up-regulate T cell function by releasing immunosuppression mediated by co-inhibitory molecules such as CTLA-4, PD-1/PD-L1, TIM-3, LAG-3, BTLA or other factors.

Up-regulate immune response by approach 1 can be easily archived by using agoistic antibodies binding to CD28 or other co-stimulatory molecules.

However, it is widely believed in the medical field that the agoistic antibodies such as anti-CD28 antibodies have a very high safety risk, as catastrophic result showing in a phase I clinic study of anti-CD28 monoclonal antibody drug (code: TGN1412) in England in 2006, in which 6 healthy subjects had an extremely severe adverse reaction to this drug on the day of infusion. (Suntharalingam G, et al, N Engl J Med 2006; 355: 1018-1028)

On the contrary, the antagonistic monoclonal antibody drug eliminating or reducing the immunosuppression mediated by CTLA-4 or PD-1/PD-L1 and other factors has been the most successful focus in the research and development of anti-tumor drug world-wide, owing to its distinctive anti-tumor curative effect and acceptable safety shown in multiple international clinic studies; the development of anti-tumor drugs targeted PD-1/PD-L1 is particularly remarkable. (Quezada S A and Peggs K S: British Journal of Cancer 2013; 108: 1560-1565; Flemming A: Nat Rev Drug Discov. 2012, 11:601).

PD-1 gene was first discovered and cloned by Tasuku Honjo and his colleagues in 1992, and it has one IgV-like domain in the extracellular region thereof with 23% homology to CTLA-4 (Ishida, Y., Agata, Y, Shibahara, K. and Honjo, T.: EMBO J. 1992; 11:3887).

PD-1 is mainly expressed on activated T lymphocyte, B lymphocyte, mononuclear and other immune cells (Yasutoshi Agata et al, International Immunology 1996; 8: 675). There are two receptors or ligands of PD-1: PD-L1 (Freeman G J et al, JEM 2000; 192: 1027-1034), also known as B7-H1 (Dong H et al, Nature Medicine 1999; 5: 1365-1369), and PD-L2 (Latchman Y et al, Nat. Immunol. 2001; 2: 261-268), also known as B7-DC (Tseng S Y et al, JEM 2001; 193: 839-845). PD-L1 and PD-L2 are mainly expressed on target cell such as tumor cell or antigen presenting cell (Thompson R H et al, Cancer Res 2006; 66: 3881-3885).

The phenomenon of PD-1 participating in the down-regulation of in-vivo immunologic function was first observed by Tasuku Honjo and his colleague in PD-1 knockout mice. They found that PD-1 knockout mice developed lupoid glomerulonephritis and arthritis (Nishimura H et al: Immunity 1999; 11:141) in C57BL/6 background, while in Balb/c background, developed high titer anti-cardiac muscle tissue antibody, thereby causing severe auto-immune cardiomyopathy (Nishimura H. et al: Science 2001; 291:319).

Normal tissues or cells in vivo can be prevented by PD-L1 or PD-L2 expressed therein from being attacked or killed and rejected by peripheral lymphocytes (Keir M. E. et al: J Exp Med 2006; 203: 883-895; Keir M E, Butte M J, Freeman G J, Sharpe A H: Annu Rev Immunol 2008; 26: 677-704).

Unfortunately, mutated tumor cells can also up-regulate the expression of PD-L1 or PD-L2 to bind with PD-1 on lymphocytes and inhibit the function of lymphocytes to evade immune attack or killing and rejection to keep growing (Dong H et al, Nature Medicine 2002; 8: 793-800; Azuma T et al, Blood 2008; 111: 3635-3643). The neutral PD-1 or PD-L1 given in-vivo to block the binding of PD-1 on lymphocytes to PD-L1/PD-L2 on tumor cells, can restore the function of lymphocytes to immunologically recognize and kill mutated tumor cells, thus to suppress tumor growth and even eradicate or reject tumor cells (Iwai Y et al, PNAS 2002; 99: 1229; Hirano F et al, Cancer Res 2005; 65: 1089-1096).

Based on these previous fundamental studies and encouraging preclinical animal experiment results, many international pharmaceutical enterprises such as Bristol-Myers Squibb (BMS)/Medarex, Merck and Genentech have started the development of new antibody drugs for the purpose of blocking the binding of PD-1 to its ligand PD-L1 and have applied for relevant patents since 2003.

For example, in a US inventive patent document for the authorized U.S. Pat. No. 8,008,449, Medarex and Ono Pharmaceutical disclosed such hybridomas of anti-human PD-1 antibody as screened by cross-immunizing HuMab Mouse with human Ig with transfected CHO cells and such human PD-1 proteins of full length or with extracellular domain as expressed thereby as mixed antigen, antibody proteins secreted thereby, and nucleotide sequences thereof coding antibody proteins, as well as application of such antibody in PD-1 protein detection and treatment of cancer and other diseases.

In a US inventive patent document for the authorized U.S. Pat. No. 8,168,757, Merck Sharp & Dohme Corporation ("Merck") also disclosed multiple hybridomas of anti-human PD-1 antibody screened by immunizing the mouse with DNA consisting of PD-1, antibody protein secreted thereby, and coding nucleotide sequences thereof, and that such antibody is used for the purpose of treating cancer and infectious diseases by enhancing immunologic function in vivo.

In a US inventive patent document for the authorized U.S. Pat. No. 8,217,149, Genentech disclosed the antibody protein fragments of multiple anti-human PD-L1 obtained by screening and proliferating from the phage display, coding nucleotide sequences thereof and the purpose thereof.

These international pharmaceutical enterprises also filed inventive patent applications for PD-1 with the State Intellectual Property Office (SIPO) in China. In the patent application document No. 200680028238.9 for such anti-PD-L1 human monoclonal antibody of Medarex as entered China via the international PCT application (PCT/US2006/026046), disclosed was such monoclonal antibody specifically binding with human PD-L1 with high affinity as screened by the company out of immunized mice, the coding DNA sequence thereof and methods with which the company uses such antibody to treat cancer, infectious and other diseases.

In the inventive patent document for the patent No. 201010170022.4 on anti-PD-1 antibody and purposes thereof, Weythe and Medimmune disclosed the fragment of such anti-PD-1 antibody as screened from phasmid scFv display library, coding DNA sequence thereof and application of such antibody as pharmaceutical ingredient in treating autoimmune disease, allergic reaction, cancer and other diseases related to the immune system.

In addition to foreign pharmaceutical enterprises, many domestic Chinese R&D institutions and enterprises also have successively filed the PCT or Chinese inventive patent applications for PD-1 with the SIPO since 2013. On May 27, 2013, as the first domestic institution filing the patent application for McAb PD-1, Zhengzhou University submitted a document entitled "A Fully Humanized Anti-PD-1 Monoclonal Antibody, as Well as Preparation Method and Application Thereof" of the patent application No. CN201310199947.5 with the application publication document No. CN103242448B. Disclosed in the patent application document was a fully humanized anti-PD-1 monoclonal antibody of very high affinity and very low immunogenicity for PD-1, as well as the heavy-chain and light-chain amino acid sequences thereof. Further described in the document was the application of such fully humanized anti-PD-1 monoclonal antibody in specifically blocking PD-1/PD-L inhibiting signals, enhancing and accelerating the recovery of incapacitated cytobiological function in vivo, intensifying the killing ability of lymphocytes against tumor antigens, invasive viruses, etc, improving body immunity and timely eliminating tumor cells and viruses. The patent was authorized on Jan. 14, 2015, but was terminated due to arrears of annual fee on Jul. 20, 2016.

Below are several inventive patent applications for the McAb PD-1 filed by other domestic research institutions and enterprises ranking highly on the application list:

On Jun. 26, 2013, TopAlliance Biosciences Inc. and Suzhou Junmeng Biosciences Inc. filed the document entitled "An Anti-PD-1 Antibody and Application Thereof" of the joint patent application No. CN201310258289, disclosing a new PD-1 antibody or functional fragment thereof, and the purpose of the antibody in the preparation of medicine for cancer treatment.

On Sep. 13, 2013, BeiGene filed a document entitled "An Anti-PD-1 and the Application thereof as a Therapeutic Agent and Diagnostic Agent" of the patent application No. CN201380079581.6 with the patent application publication document No. CN105531288A), providing PD-1, Pdcd-1 or CD279, inhibiting the cell signaling and activity mediated by PD1 in immune cells, and binding with a set of amino acid residue antibodies required for the ligand of PD1 and the application of these antibodies in treating or diagnosing such cancer, infectious disease or other pathological symptoms as regulated by the function mediated by PD-1.

On Oct. 25, 2013, Stainwei Biotech Inc. filed a document entitled "A Monoclonal Antibody Antagonizing and Inhibiting the Binding of PD-1 to Its Ligand, as Well as Coding Sequence and Application Thereof" of the patent application No. CN201310512512.1 with the patent application publication document No. CN104558177A, disclosing a mouse monoclonal antibody antagonizing and inhibiting the binding of PD-1 to its ligand and the heavy-chain and light-chain variable region amino acid sequences thereof, the DNA molecular nucleotide sequence coding the heavy-chain and light-chain variable regions of such antibody, as well as the preparation method of human-mouse chimeric antibody of such antibody and a derivative thereof and the application thereof in PD-1 protein detection.

On Nov. 14, 2013, Shanghai Hengrui Pharmaceutical Co., Ltd. and Jiangsu Hengrui Medicine Co., Ltd. filed a document entitled "PD-1, Fragment Antigen Binding and Medical Application Thereof" of the patent application No. CN201480011008.6 with the patent application publication document No. CN105026428A.

Most of the patent applications above and the patent applications for PD-1 antibody thereafter are in the stage of document disclosure or substantive examination.

On Oct. 28, 2015, the patent application entitled "A PD-1 Human Monoclonal Antibody and the Way to Treat Cancer with Anti-PD-1 Antibody" filed by Ono Pharmaceutical of Japan and Medarex was duly authorized by the SIPO with the authorized patent No. CN103059138B. The authorized patent protects the PD-1 human monoclonal antibody restricting the specific antibody structure of CDR sequence and the way to cure cancer with such PD-1 antibody.

In terms of the global development of PD-1/PD-L1 drugs, so far, only the following three antibody drugs have been approved by the FDA:

1) Opdivo (generic name: Nivolumab, former code: BMS-936558, MDX-1106) is a fully humanized PD-1 McAb (IgG4-kappa) jointly developed by Bristol-Myers Squibb/Medarex and Ono Pharmaceutical. In July 2014, it was first approved for the treatment of end-stage melanoma in Japan, and thus became the first PD-1 inhibitor drug approved for marketing in the world. On Dec. 12, 2014, Opdivo (Nivolumab) was approved by the FDA for the first-line treatment for patients with melanoma that responds to no other drugs, is unresectable by operation or metastatic.

2) Anti-PD-1 McAb drug Keytruda (generic name: Pembrolizumab, former code: MK3475, lambrolizumab) is a humanized PD-1 McAb (IgG4-kappa) developed by Merck. On Sep. 4, 2014, through the fast-tracking passage for approval of the FDA, it was first approved for treating patients with end-stage melanoma, and having received Ipilimumab (anti-human CTLA4 McAb) treatment, or having received BRAF inhibitor treatment for carrying BRAF gene mutation, and thus became the first anti-PD-1 drug approved for marketing in the USA.

3) Tecentriq (generic name: Atezolizumab, former code: MPDL3280A) is a humanized PD-L1 McAb (IgG1-kappa) developed by Genentech/Roche, and was first approved for marketing as a second-line drug for end-stage bladder cancer by the FDA on May 19, 2016.

In the EU, Opdivo (Nivolumab) and Keytruda (Pembrolizumab) were approved for marketing in June and July 2015, respectively.

In China, so far no PD-1 or PD-L1 McAb drug has been approved for marketing yet.

All the aforesaid two PD-1 McAb drugs and one PD-L1 McAb drug approved for marketing in the US, EU or Japan and other countries/regions showed clinical benefit response of suppressing tumor growth, and even wiping out and rejecting tumor, and significantly prolonging the survival time of patients during their own early clinic-testing stage (Phase I), with acceptable safety for long-term usage (Brahmer J R et al, JCO 2010; 28: 3167-3175; Topalian S et al, NEJM 2012; 366: 2443-2454; Brahmer J R et al, NEJM 2012; 366: 2455-2465; Hamid 0 et al, NEJM 2013; 369: 134-144). The most sensational, large clinic-testing result first public reported was the one disclosed by Topalian et al in the internationally medical magazine N Engl J Med in June 2012 (Topalian S et al: N Engl J Med 2012, 366: 2443-2454). According to the article, in the Phase I clinic study involving 296 end-stage malignant tumor patients, after the patients were intravenously injected with Nivolumab (code: BMS-93655), a PD-1 McAb drug developed by BMS every two weeks, 28% of melanoma patients, 27% of renal cell carcinoma patients and unexpectedly 18% of NSCLC patients saw their tumors inhibited or shrunk. Nivolumab also showed long lasting clinical effects of tumor treatment. For instance, among 31 patients followed up for over one year, 20 (64.5%) remain effective clinically.

Subsequent study further showed that the curative effect of Nivolumab was even better than that of chemotherapy drugs in clinic treatment of end-stage malignant tumor. For example, according to an article published by Robert et al in the magazine N Egnl J Med (Robert C et al: N Engl J Med. 2015; 372:320-30) in January 2015, in a clinical study called CheckMate066 sponsored by BMS, 418 such patients with end-stage metastatic melanoma and without BRAF mutation as untreated and grouped randomly took Nivolumab once two weeks or the chemotherapy drug dacarbazine, and after such treatment for one year, compared with the group treated with dacarbazine, there was significant improvement in overall survival and progression-free survival of patients in the Nivolumab treatment group. The overall survival rate of the Nivolumab treatment group was 72.9%, while that of the dacarbazine treatment group was 42.1% ($P<0.001$); the median progression-free survival of the Nivolumab treatment group was 5.1 months, while that of the dacarbazine treatment group was 2.2 months ($P<0.001$); the objective remission rate of the Nivolumab treatment group was 40%, while that of the dacarbazine treatment group was 13.9% ($P<0.001$).

Similar to numerous clinical study results of Nivolumab, clinical study results of Pembrolizumab are also amazing and inspiring. According to an article reported by Hamid et al in N Egnl J Med (Hamid 0 et al: N Engl J Med 2013, 369:134-144) in July 2013, in the Phase I of a international multicenter trial, end-stage melanoma patients with progress in their disease after receiving Ipilimumab treatment at least twice were allocated at random to be intravenously injected with 2 mg/kg or 10 mg/kg Pembrolizumab once three weeks, until there was any progression of disease or intolerant toxicity, or the patients volunteered to withdraw from the study. By analyzing the study results, it's found that 38% of the patients saw their tumor inhibited or shrunk after Pembrolizumab treatment; among 52 cancer patients with the median follow-up time of 11 months, 42 (81%) still held good and continued to receive the Pembrolizumab treatment.

According to an article published by Robert C et al in the international magazine Lancet (Robert C et al: Lancet. 2014 Sep. 20; 384:1109-17) in September 2014, 173 end-stage melanoma patients having received ineffective Ipilimumab treatment were grouped at random to be intravenously injected with Pembrolizumab (dosage: 2 mg/kg, n=89) or Pembrolizumab (dosage: 10 mg/kg, n=84) once three weeks, until there was any progression of disease or intolerant toxicity, or the patients volunteered to withdraw from the study. The results showed that, the median follow-up time was 8 months, ORR of two McAb Pembrolizumab dosage groups was 26%, among which 21 out of 81 patients in the 2 mg/kg group sand 20 out of 76 patients in the 10 mg/kg group survived, respectively.

Despite revolutionizing treatment in cancer, clinically there are still many deficiencies of McAb drugs Opdivo (Nivolumab) and Keytruda (Pembrolizumab), including but not limited to, the following issues:

1) McAb drugs of Opdivo (Nivolumab) and Keytruda (Pembrolizumab) have only been approved for clinic treatment of a few types of tumor such as end-stage melanoma, renal carcinoma, NSCLC, HNSCC and bladder cancer, and the safety and validity of clinical treatment of other common and multiple malignant tumors with such drugs are to be studied and verified.

2) With regards to the types of tumors of which the treatment with McAb drugs Opdivo (Nivolumab) and Keytruda (Pembrolizumab) has been approved, the effective rate of treatment of such drugs lies in 15-50% only, and median PFS of patients only lasts for several months, meaning that, for most cancer patients, even if they have taken current PD-1 McAb drugs, there is no guarantee that they can be benefited or their survival time can be prolonged significantly.

3) Patients long-term using McAb drugs Opdivo (Nivolumab) and Keytruda (Pembrolizumab) may suffer from immune-related adverse events such as immune-mediated pneumonitis; the said adverse events sometimes may involve skin, gastrointestinal tract, liver, internal secretion and many other tissues and organs (Naidoo J et al: Ann Oncol. 2015; 26:2375-91).

In order to overcome the aforesaid deficiencies, in addition to further carry on fundamental and clinical studies on the specific epitope, mode of action, causes of adverse drug reaction, etc of the existing drugs Opdivo (Nivolumab) and Keytruda (Pembrolizumab), novel anti-PD-1 McAb drugs with unique antigen binding region/epitope and higher biological activity/anti-tumor effec than the existing Opdivo (Nivolumab) and Keytruda (Pembrolizumab) in-vitro and in-vivo need to be developed and launched clinically, thus to meet the medical needs by numerous patients with cancer, either in China and abroad.

As the binding of PD-1 to its ligand (PD-L1 or PD-L2) is characterized by extensive binding domain involved, with more than dozens of amino acid sites engaging in the binding, etc, and since human PD-1 protein shares only 60% homology with mouse PD-1 protein in amino acid sequence, it is speculated theoretically that, it is possible to make or develop various novel anti-PD-1 McAbs with a specific binding domains/differen epitopes by using traditional mouse immunization and hybridoma technology. These McAbs, with theie new and unique antigen binding domains or epitopes, are expected to have a stronger in-vitro and in-vivo biological activity or to have a safer and more superior curative effects than currently marketed PD-1 McAb Opdivo (Nivolumab) or Keytruda (Pembrolizumab). On the one hand, these new McAbs, can be used as pharmaceutical ingredients, either in combination or sequence with marketed PD-1 McAb drugs or PD-L1 McAb drugs, to further enhance host immunologic function and anti-tumor effect. On the other hand, these new McAbs are expected to be developed into novel immune function enhancers or used alone as anti-tumor pharmaceutical preparations.

SUMMARY

One of the technical issues to be solved by the invention is to provide a novel anti-PD-1 McAb or a derivative thereof such as antibody Fab fragment and single-chain antibody, with antigen binding domains or epitopes different from those of current Opdivo (Nivolumab) or Keytruda (Pembrolizumab). The McAb or derivative thereof can antagonize and inhibit the binding of PD-1 antigen to its ligands (PD-L1 and PD-L2).

The second technical issue to be solved by the invention is to provide DNA molecules or genes encoding the aforesaid antibody.

The third technical issue to be solved by the invention is to provide drugs or pharmaceutical compositions containing the aforesaid antibody.

The fourth technical issue to be solved by the invention is to provide the application of drugs or pharmaceutical compositions containing the aforesaid antibody in tumor treatment.

The fifth technical issue to be solved by the invention is to provide the preparation method of the aforesaid antibody.

In order to solve the above-mentioned technical issues the invention applies the following technical solutions:

Firstly, the invention provides a novel anti-PD-1 McAb or a derivative thereof such as antibody Fab fragment or single-chain antibody, with antigen binding sites or epitopes different from those of Opdivo (Nivolumab) or Keytruda (Pembrolizumab). This novel antibody consists of the first and the second variable regions: the first variable region is an antibody light chain variable region, of which the antigen CDR1, CDR2 and CDR3 are the amino acid sequences shown in SEQ ID NO: 3, SEQ ID NO: 4 and SEQ ID NO: 5, respectively, while the second variable region is an antibody heavy chain variable region, of which the antigen CDR1, CDR2 and CDR3 are the amino acid sequences shown in SEQ ID NO: 8, SEQ ID NO:9 and SEQ ID NO: 10, respectively.

The said antibody includes humanized monoclonal antibody, and the said derivative thereof includes antibody Fab fragment, single-chain antibody, bi-specific antibody, etc.

As the preferred technical solution of the invention, the said first variable region is an antibody light chain variable region, with the amino acid sequence shown in SEQ ID NO: 11, while the said second variable region is an antibody heavy chain variable region, with the amino acid sequence shown in SEQ ID NO: 12.

As the preferred technical solution of the invention, it contains the said antibody light chain variable region and human antibody light chain constant region, as well as the hinge region, CH1, CH2 and CH3 of the said antibody heavy chain variable region and human antibody heavy chain constant region.

As the preferred technical solution of the invention, the said human antibody light chain constant region is from the human antibody kappa chain or the antibody lamda chain, and the said human antibody heavy constant region is from the human subtype IgG1, IgG2, IgG3 or, preferably IgG4.

Secondly, the invention provides a DNA molecule or gene nucleotide sequence coding the said antibody or the derivative thereof, of which the antibody light chain variable region gene nucleotide sequence is shown in SEQ ID NO: 13, and the antibody heavy chain variable region gene nucleotide sequence is shown in SEQ ID NO: 14.

Thirdly, the invention provides an expression vector, which contains the DNA molecular/gene nucleotide sequence coding the said antibody or derivative thereof, and the expression regulation sequence operably linked thereto.

Fourthly, the invention provides a recombinant host cell, which is transformed from the said expression vector. The reconstitution host cell or daughter cell thereof expresses the said antibody or the derivative thereof. The antibody includes humanized monoclonal antibody, and the derivative thereof includes antibody Fab fragment, single-chain antibody and bi-specific antibody.

Fifthly, the invention provides a medicine or pharmaceutical composition, which contains a pharmaceutically effective amount of the antibody or the derivative thereof and a pharmaceutically acceptable carrier.

Sixthly, the invention provides the application of the medicine or pharmaceutical composition of the aforesaid antibody in preparing the medicine for treatment of tumor, preferably colon cancer. In its specific embodiments, the invention describes the application of the humanized antibody in inhibiting colon cancer growth in vivo.

Seventhly, the invention provides a method for preparing such antibody or the derivative thereof, which includes the following steps:

a) Provide an expression vector containing the DNA sequence and the expression regulation sequence operably linked thereto;

b) Transform host cells with the expression vector set forth in step a);

c) Culture host cells got from step b) under the conditions suitable for the expression of the said antibody; and d) Get the said antibody by the separation and purification of the host cell culture fluid.

The term "monoclonal antibody (McAb)" herein refers to immune globulins obtained from a pure-line cell, which have the same structure and chemical properties and is specific to single antigenic determinant. Different from conventional polyclonal antibody preparations (with different antibodies specific to different determinants in general), each monoclonal antibody is specific to single determinant on antigen. In addition to the specificity thereof, monoclonal antibodies have the advantage that they are cultured from hybridomas or recombination engineering cells without any mixture of other immune globulins. The modifier "monoclonal" shows the character of the antibody that it comes from a homogeneous antibody cluster, which should not be interpreted as it needs any special methods to generate antibodies.

The term "humanization monoclonal antibody" herein refers to a murine monoclonal antibody of which all or substantially all amino acid sequences except complementarity-determining regions (CDR) and including framework region sequences in variable region are replaced with amino acid sequences of human immune globulin to furthest reduce the immunogenicity of the murine monoclonal antibody.

The terms "antibody" and "immune globulin" herein are 15,000-or-so-dalton heterogenous tetramer glycoproteins with the same structure features and consisting of two same light chains (L) and two same heavy chains (H). Each L is connected with H by a covalent disulfide bond, while the number of disulfide bonds between isotypic Ls varies with each immune globulin. Every H and every L have intrachain disulfide bonds at regular spaces. On an end of each H, there is a $V_H$, followed by multiple constant regions; on both ends of each L, there are $V_L$ and constant regions; constant regions of L faces the first constant region of H, while the $V_L$ faces the $V_H$. Special amino acid residues form an interface between $V_L$ and $V_H$.

The term "variable" herein means that the difference of some sections of variable regions of the antibody in sequence makes various specific antibodies bind with and specific to specific antigens thereof. However, variability is not distributed evenly in the whole variable region of the antibody, but concentrated in three such fragments of $V_L$ and $V_H$ as become the CDR or HVR. The relatively conservative part of the variable region is framework region (FR). $V_H$ and $V_L$ of the antibody each consist of four FRs, which are roughly in the β-folded configuration connected by three CDRs forming a joining link, and may partly form the β-folded structure in some cases. CDRs of each chain are close together via FRs and form the antigen-binding site of the antibody together with the CDRs of the other chain (Kabat et al, NIH Publ. No. 91-3242, Vol. 1, Page 647-669 (1991)). Constant regions of the antibody doesn't participate in the binding of antibodies to antigens directly, but show different effector functions, such as engaging in antibody-dependent cellular cytotoxicity (ADCC) or complement-dependent cytotoxicity (CDC) of the antibody.

In general, the antibody of the invention can be prepared with the following method:

First, insert the gene coding the antibody of the invention into the expression vector with suitable expression regulatory sequences.

The term "expression regulatory sequence" herein usually refers to the sequence participating in the control of gene expression. Expression regulatory sequence includes such promoters and termination signals as operably connected with target genes. DNA sequences coding the antibody of the invention can be obtained with conventional methods well known by technicians in the field, such as artificial synthesis according to protein sequences disclosed in the invention or PCR proliferation. Then, the DNA fragments so acquired can be inserted into suitable expression vectors with methods well known in the field. Expression vectors used in the invention can be those sold in the market and known by the technicians in the field, such as pCDNA3.1 of Invitrogen.

Host cells suitable for being transformed by expression vectors generally include prokaryotic cell and eucell. Common prokaryotic host cell includes *Escherichia coli* and *Bacillus subtilis*; common eukaryotic host cell includes yeast cell, insect cell, mammalian cell. In the invention, the preferable host cell is mammalian cell, especially CHO cell.

Get the culture supernatant fluid after culturing host cells transformed by expression vectors under suitable conditions such as adherent or suspension culture with serum-free medium in the cell culture bottle or bio-reactor, and then get the antibody of the invention after purification with conventional separation steps or methods well known by technicians in the field, including protein-A affinity chromatography, ion-exchange column chromatography and filtration sterilization.

The antibody of the invention got by purification can be dissolved in sterile saline solution and other suitable solvents, with the concentrations of 0.01-100 mg/ml, ideally, 1-20 mg/ml).

In order to obtain murine monoclonal antibodies antagonizing and inhibiting the binding of PD-1 (programmed death-1) to its ligand, hybridoma cell lines were generated by immunizing mice with recombined human PD-1 extracellular protein through repetitious subcutaneously immunization in a small dose, followed by screening polyclonal antibodies with high potency against PD-1 protein and then generating numbers of hybridomas that stably secreted anti-human-PD-1 mAb by fusing spleen cells taken from immunized mice mouse with mouse myeloma cells in-vitro. After drug-selection, subcloning and screening by ELISA, western blotting, immunohistochemistry, etc, one mouse hybridoma cell line No. Ab21 was identified e not only specifically binding to human PD-1 protein, but also capable of blocking/inhibiting the binding of PD-1 protein to its ligands PD-L1 and PD-L2.

The invention gets the gene fragment en-coding the heavy chain variable region and the light chain variable region of this murine antibody by means of genetic engineering, etc., thereby conducting the humanization transformation of the antibody and establishing the expression vector thereof (pCDNA3.1-hAB21). Get re-engineering cells stably and efficiently secreting humanization antibody by introducing the expression vector into CHO cells after transfection, and bioactive humanized hAb21 protein are obtained through separation and purification of culture supernatants from the reengineering cells.

The competitive ELISA analysis shows that the PD-1 binding epitope of humanized hAb21 is remarkably different from that of Nivolumab or Pembrolizumab (MK3475). The humanized hAb21 has inhibiting effect on tumor growth after administration in vivo, and apparent has a much better curative effect than that of marketed drug Pembrolizumab (MK3475).

BRIEF DESCRIPTION OF THE DRAWINGS

FIG. 1 is the diagrammatic drawing of a comparative analysis of human PD-1 and mouse PD-1 amino acid sequences in example 1 of the invention.

FIG. 2 is the diagrammatic drawing of the ELISA results, showing the binding of cell culture supernatant samples from mouse hybridomas to recombinant PD-1 extracellular protein pre-coated on 96-well plate in example 1 of the invention. mAB21 and mAbl1 are the supernatant samples from two different hybridomas, and the non-fused SP2/0 myeloma cell culture sample is served as the negative control.

FIG. 3 is the diagrammatic drawing of flow-cytometry (FCM) results, showing the binding of mouse antibody samples to CHO cells stably transfected with human PD-1 gene (CHO/PD-1) in example 2 of the invention. FIG. 3A represents sample from control-IgG, set as a negative control.

FIG. 3B represents sample from PDL2-Fc fusion protein, set as a positive control.

FIG. 3C represents sample from hybridoma mAb7 supernatant.

FIG. 3D represents sample from hybridoma mAB21 supernatant.

FIG. 4 is the diagrammatic drawing of the immunohistochemistry (IHC) results, showing the specific binding of mAB21 McAb sample to tissue-sections in example 3 of the invention.

FIG. 4A represents monkey spleen tissue section.

FIG. 4B represents monkey lympho-node tissue section.

FIG. 6A is the diagrammatic drawing of a comparative analysis of amino acid sequences in the light chain variable region of humanized hAb21, Nivolumab and MK3475 in example 8 of the invention. Boxed areas are amino acid sequences in CDR1, CDR2 and CDR3.

FIG. 6B is the diagrammatic drawing of a comparative analysis of amino acid sequences in the heavy chain variable regions of humanized hAb21, Nivolumab (Nivo), and MK3475 in example 8 of the invention. Boxed areas amino acid sequences in CDR1, CDR2 and CDR3.

DETAILED DESCRIPTION OF THE EMBODIMENTS

Figure 5A:
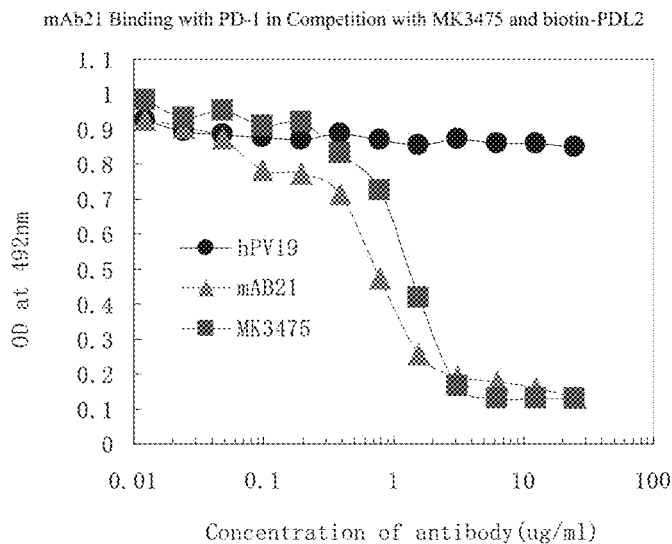
FIG. 5A is the diagrammatic drawing of in-vitro competitive ELISA result, showing the antagonizing and blocking of the binding of biotin-PDL2-Fc protein to human PD-1 protein pre-coated on 96-well plates by mAB21 or MK3475 as described in example 4 of the invention. hPV19 is an irrelevant McAb sample, set as the negative control.

The following is the further description of the invention in combination with several embodiments, which are used to illustrate rather than restricting the invention.

Example 1. Generation, Screening and Identification of Murine Hybridoma Cell Lines that Secrete Anti-PD-1 Antibodies 1) Comparative Analysis of the Amino Acid Sequences of Human PD-1 and Mouse PD-1 Protein Please refer to FIG. 1 for comparison and analysis of the amino acid sequences of human PD-1 proteins and mouse PD-1 proteins; amino acid sequences marked in italics in the box are signal peptides that guide extra-cellular secretion and expression of PD-1, and amino acid sequences marked in bold in the box are the transmembrane region (TM) of PD-1 proteins. As shown in FIG. 1, in respect of amino acid sequences, human PD-1 protein and mouse PD-1 protein overall share 60% in homology only, while there are over thirty (30) amino acid differential points in the extra-cellular region (including IgV region) which participates in recognizing and binding the ligand thereof directly in the human and mouse. It is thus speculated that, a McAb of mouse anti-human PD-1 for a variety of different binding regions or amino acid epitopes can be generated through application of the traditional antigen protein antigen immunization in mouse and hybridoma preparation technology. These anti-human PD-1 McAbs, with antigen the binding regions or epitopes different from those of the current PD-1 McAbs such as Opdivo (Nivolumab) or Keytruda (Pembrolizumab), are expected to have different or even superior biological activity in vitro and vivo and curative effects than those of Opdivo (Nivolumab) or Keytruda (Pembrolizumab). On the one hand, acting as the ingredient of drug, these new McAbs recognizing new epitopes, can be used as drug ingredient, either in combination or sequence of the current PD-1 McAb drug or PD-L1 McAb drug to further enhance immunologic function of the organ and improve the anti-tumor effect, and, on the other hand, be developed independently to become a new type immune function enhancer or antitumor drug preparation which can be used alone.

Hence, the invention carries out the development and preparation of this kind of new PD-1 McAb, with detailed preparation procedures as follows:

2) Generation, Screening and Identification of Murine Hybridoma Cell Lines that Secrete Antibodies Antagonizing PD-1

Step 1. Source of Recombination Human PD-1 Protein (Immunizing Antigen) and Immunization of Animals In the example of the invention, the antigen for immunization is a recombined PD-1 extracellular protein expressed by mammal cells (a product from Sino Biological Inc.). After mixing with Freund's complete adjuvant (FCA) (a product from Sigma Corporation), then inject at multiple sites in the skin of Balb/c mice (100 μl per mouse and 10 μl PD-1 protein each time). 2 to 3 weeks after this first immunization, inject a mixture of human PD-1 proteins and FCAs (a product from Sigma Corporation) again at multiple sites. After boost immunization for 3 to 4 times, collect an aliquot of mouse sera and test the activity of antibodies antagonizing PD-1 in mouse sera by ELISA in 96-well plate pre-coated with recombined PD-1 human PD-1 protein, and then get cells from the spleen in those mice showing higher anti-PD-1 activity, for preparation of cell fusion in the next step.

Step 2. Cell Fusion 3 to 4 days after the last immunization, mouse spleen cell suspensions were prepared and fused with mouse SP2/0 myeloma cell (purchased from Cell Preservation Center of Shanghai Faculty of Life Sciences, CAS) at a ratio of 5:1 or 10:1 under the action of 50% PEG-1000 (a product from Sigma Corporation). Cell-fusion was done by adding PEG of 1 ml according to the conventional method (Kohler G. and Milstein C: Nature 1975; 256:495-497), which should be finished in 60 s. After reaction occurred for 90 s, the fusion was terminated by adding serum-free RPMI-1640 culture medium, centrifuging at the rate of 1000 rpm for 10 minutes, then discard the supernatant, and resuspending pellet cells to an concentration at $1 \times 10^6$ cells/ml with RPMI 1640-10% HAT (H stands for the hypoxanthine, A the aminopterin, and T the thymidine, a product from Sigma Corporation) FCS culture medium, apply the 96-well culture plate (200 μl per well), and culture for 2 to 3 weeks in the 5% CO2 incubator (a product from Thermo Corporation) at 37° C.

Step 3. Screening Mouse Hybridoma Cells that Positively Secrete Antibodies by ELISA Similarly, coat the 96-well plate with the recombination human PD-1 protein (2 μg/ml, pH 9.6, 0.1 M NaHCO3 fluid), and add 2% BSA and seal at 4° C., after coating at 37° C. for 2 hours.

On the next day, after washing the coated plate with PBS-0.1% Tween20, add hybridoma cell culture supernatants to be detected (with the non-fused SP2/0 myeloma cell culture supernatants as the negative control) to the 96-well plate and incubate for 2 hours at 37° C. After washing with PBS-0.1% Tween20, then add the HRP-labeled goat anti-mouse IgG (a product from Sigma Corporation), to the 96-well plate and incubate for 2 hours at 37° C. After sufficient washing with PBS-0.1% Tween20 again, add substract (OPD-0.1% $H_2O_2$) for color development for 10-15 min and then add 0.1M HCl solution to terminate the reaction. Afterwards, the OD value was measured at 492 nm in the MK3-Multiskan ELISA (a product from Thermo Scientific Corporation). Hybridoma cells with OD 492 value 5-10 times higher than the negative control were subcloned again as well as amplified and cryopreserved.

Step 4. Subcloning and Limiting Dilution Assay of Positive Hybridoma Cells

After primary screening, dilute the positive hybridoma cells to 1-10 cells/well with RPMI-1640-10% FCS culture medium, seed into 96-well cell culture plate, and culture in the 5% CO2 incubator at 37° C. for 2 to 3 weeks. After cloning and growing, collect supernatants and assay for anti PD-1 mAb with ELISA again. FIG. 2 is the diagrammatic drawing of the ELISA results showing the binding of the supernatants from subcloned hybridoma cells to recombination PD-1 proteins. Supernatants from hybridoma cell line mAB21 showed binding to PD-1.

Example 2. Flow-Cytometry (FCM) Analysis of the Binding of Murine mAB21 to CHO/PD-1

In the example, to detect the binding of mAB21 to CHO cells stably expressing human PD-1 (CHO/PD-1) by flow-cytometry, murine mAB21 supernatant, or murine mAB7 supernatant (which is known to bind to human PD-1 proteins, as described in the public document of Chinese patent application, CN104558177A) were used as the first antibody, and the FITC labeled goat anti-mouse IgG as the second antibody. For this purpose, CHO-PD-1 cells were incubated with mouse IgG (negative control, A), human PDL2-Fc fusion proteins (B), mAB7 supernatants (C, 1:5 dilition) or mAB21 liquid supernatants (D, 1:5 dilition) respectively; after one-hour incubation at 4° C. and washing with PBS-0.1% FCS, add FITC-labeled goat anti-mouse IgG (a product from Sigma Corporation) (for human PDL2-Fc fusion protein samples, add FITC-labeled goat anti-human IgG-Fc); after one-hour incubation at 4° C. and washing with PBS-0.1% FCS again, the samples were subjected to flow-cytometry analysis (Cytomics FC500 MCL) (a product of Beckman Coulter Corporation).

FIG. 3 is the diagrammatic drawing of the representative FCM results. As shown in FIG. 3, compared with the negative control sample of mouse IgG (FIG. 3A), human PDL2-Fc fusion protein sample (FIG. 3B), mAB7 supernatant positive sample (FIG. 3C) or tested sample mAB21 supernatant (FIG. 3D) all show the specific binding to CHO/PD-1 cells; the binding intensity of mAB21 sample is higher than that of mAB7.

Example 3. Immunohistochemistry (IHC) Analysis of the Binding of mAB21 to Macaca fascicularis Tissues In the example, the binding of mAB21 to normal monkey tissues (provided by JOINN Laboratories (Suzhou)) was detected by immunohistochemistry (IHC). After rehydration and antigen exposure, mAB21 supernatants were added into the paraffin sections of monkey spleen and lympho-node tissues. After one-hour incubation at normal temperature and washing, add DAB to let the color to develop, then counterstain with hematoxylin, mount and take photos. FIG. 4 is the representative IHC results, showing the specific binding of mAB21 to the monkey spleen (FIG. 4A) and lympho-node tissues (FIG. 4B).

Example 4. Competitive ELISA to Detect mAB21 Antagonizing and Inhibiting the Binding of PD-1 Protein to its Ligands One way to detect the biological activity of mAB21 in-vitro is to use a competition ELISA method to assay the inhibition of PD-1 protein binding to the receptors (PD-L1 and PD-L2) by mAB21.

The principle and procedure of the competition ELISA method are as follows: Prepare mAB21 or positive control samples with different concentrations. For example, mix MK3475 with fixed concentrations of biotin labeled human PD-1 receptor proteins (such as PDL1-Fc or PDL2-Fc). Then transfer the mixture to the 96-well plates pre-coated with PD-1 protein, after incubation and washing, add the enzyme labeled Avidin (such as HRP labeled Avidin). After incubation and washing again, add the substance to develop color and measure OD value.

The detailed steps for this competition ELISA are as follows:
1) Coat 96-well plates with recombination human PD-1 extracellular proteins (a product from Sino Biological Inc.) at the concentration of 2 μg/ml and 50 μl/per well at 4° C., staying overnight;
2) After rinsing with PBS and 2% BSA (diluted in PBS-0.1% tween20) and sealing at the indoor room temperature, add fixed amount of biotin labeled PDL1-Fc proteins or PDL2-Fc proteins (products from Sino Biological Inc.), AB7 antibodies or the unrelated mouse IgG at different concentration and incubate for 2 hours at 37° C.;
3) After washing with PBS-T solution, add HRP labeled Avidin (1:5000), and incubate for 1 h at 37° C.;
4) After washing with PBS-T solution, add the color-substrate solution (o phenylenediamine)-3% hydrogen peroxide, and develop the color after 10 min at the indoor temperature; and
5) Add HCL to terminate the reaction, and detect the light absorption value of each well at the wave length of 492 nm.

FIG. 5A is the representative results of the competitive ELISA showing the inhibition of binding of Biotin-PDL2Fc to the PD-1 protein by the tested sample mAB21 or the positive sample MK3475. As shown in FIG. 5A, in the samples with different concentrations of mAB21 or MK3475 and the fix amount of biotin labeled PDL2-Fc protein, the OD value of each well is inversely co-related with the amount of antibody protein, i.e. the higher amount of mAB21 or MK3475 added, the lower OD value. The addition of unrelated McAb samples has less influences on the OD value. These results clearly shown that mAB21, similar to MK3475, inhibiting the binding of PD-1 to is receptor.

Example 5. ELISA Assay for Competition Binding of mAB21 and MK3475 to PD-1 Protein A similar competition ELISA method is used for the detection and analysis of competition binding of mAB21 and MK3475 to PD-1 proteins, the principle and procedure of this detection are as follows:

Mix different concentrations of mAB21 or MK3475 with fixed amount of biotin-labeled M3475 (biotin-MK3475), and transfer the mixture to the 96-well plate pre-coated by PD-1 proteins, after incubation and washing, then add enzyme labeled Avidin (such as HRP labeled Avidin), add the substrate and measure the OD value.

Figure 5B:
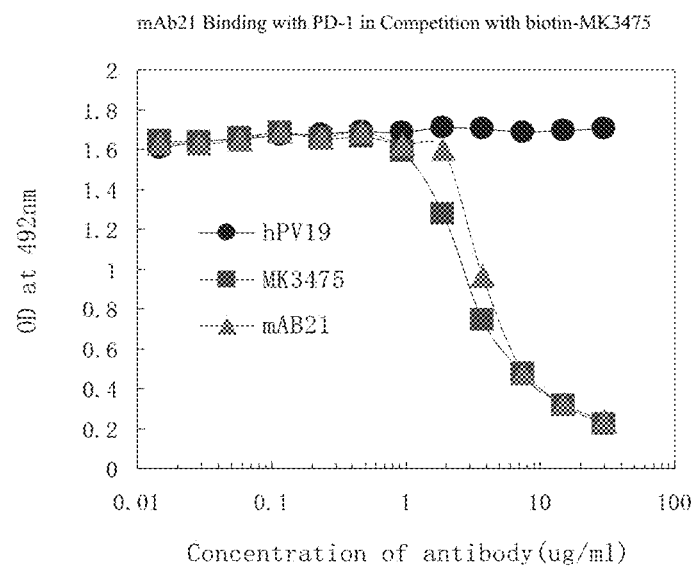
FIG. 5B is the diagrammatic drawing of in-vitro competitive ELISA result, showing the antagonizing and blocking of the binding of bitotin-MK3475 to human PD-1 protein pre-coated on 96-well plates by mAB21 or MK3475 as described in example 5 of the invention. hPV19 is an irrelevant McAb sample, set as the negative control.

FIG. 5B is the representative competition ELISA results. As shown in FIG. 5B, samples from mAB21 or the MK3475 of different concentrations with fixed amount of biotin-labeled M3475 (biotin-MK3475), the OD value of the chromogenic reaction of each well is inversely co-related with the amount of antibody protein. i.e. the higher amount of mAB21 or MK3475 added, the lower OD value. The addition of unrelated McAb samples of hPV19 has less influences on the OD value of well. These results indicated that mAB21 can compete with MK3475 for the binding to PD-1.

Example 6. Cloning of mAB21 Genes Coding the Variable Region

For this purpose, extract the total RNA from mAB21 hybridoma cells and get the gene segment of the heavy chain variable region and the light chain variable region of mAB21 through cDNA cloning and amplifying respectively by RT-PCR (Reverse transcription-polymerase chain reaction) (Wang Y et al: Degenerated primer design to amplify the heavy chain variable region from immunoglobulin cDNA. BMC Bioinformatics. 2006; 7 Suppl (4): S9), with the said RNA as the template and usage of degenerate primers. The steps to clone the cDNA gene are as follows:

Step 1.

Extract the mRNA from mAB21 hybridoma cells using a kit (a product of Beyotime Biotechnology); and Step 2.

Obtain the cDNA template in the eppendorf tube by RT-PCR.

The sequence of PCR primers (AB21-H) used for reverse transcription in the heavy chain variable region of the mAB21 is GCAAGG CTT ACA ACC ACAATC, as shown in SEQ ID NO: 16;

| reaction system of RT-PCR: | |
| --- | --- |
| primer | 2 μl |
| RNA template | 30 μl |
| 10 mins incubation at 72° C., and place on the ice for 2 mins Afterwards, add: | |
| 5 × RT-PCR reaction buffer | 10 μl |
| dNTPs | 5 μl |
| PrimeScript reverse transcriptase | 1.5 μl |
| distilled water | 1.5 μl |
| total volume | 50 μl |

Have reaction at 42° C. for an-hour, and then increase the temperature to 75° C., and then at −20° C. for 15 minutes to inactive the reaction. After that, save and reserve cDNA.

Step 3. PCR Cloning and Amplification of Genes Encoding the Light Chain Variable Region and Heavy Chain Variable Region of mAB21

A pair of primers used for cloning and amplifying the genes in the light chain variable region of the mAB21 by means of degenerate primers PCR are:

Forward primer: GAC ATT GTG ATG WCM CA, as shown in SEQ ID NO: 17

Reverse primer: CTG AGG CAC CTC CAG ATG TT, as shown in SEQ ID NO: 18

W=A or T, M=A or C.

A pair of primers used for cloning and amplifying the genes in the heavy chain variable region of the mAB21 by means of degenerate primers PCR are:

Forward primer: GTR CAG CTT CAG GAG TC, as shown in SEQ ID NO: 19 R=A or G.

Reverse primer: GTG CTG GAG GGG ACA GTC ACT, as shown in SEQ ID NO: 20

After PCR amplifying, conduct electrophoretic analysis in 1% agarose for the DNA products. After electrophoresis, cutting off the separated DNA strip for nucleotide sequencing of DNA in the light chain variable region and the heavy chain variable region of the antibody. SEQ ID NO.: 1 is the DNA nucleotide sequences of the light chain variable region; SEQ ID NO.: 2 is the DNA nucleotide sequences of the light chain variable region deduced amino acid sequences of the light chain variable region. The amino acid sequences of complementarity-determining regions (CDR) CDR 1, CDR 2 and CDR 3 of the light chain of the antibody are showed in SEQ ID NO.:3, SEQ ID NO.:4 and SEQ ID NO.:5, respectively.

SEQ ID NO.: 6 is the DNA nucleotide sequences of the heavy chain variable region and SEQ ID NO.: 7 is the deduced amino acid sequences of the heavy chain variable region. The amino acid sequences of complementarity-determining regions (CDR) CDR 1, CDR 2 and CDR 3 of the heavy chain of the antibody are showed in SEQ ID NO.:8, SEQ ID NO.:9, and SEQ ID NO.:10, respectively.

Example 7. Construction of Human-Mouse Chimeric Antibody cAB21

Fused the gene segments of the light chain variable region and the heavy chain variable region of AB21 (which was acquired from cloning and amplifying in example 6) with the gene segments of the light chain C-domain of human-kappa, and the heavy chain C-domain of human IgG1, got the human-mouse cAB21L gene and human-mouse cAB21H gene, respectively. Afterwards, inserted cAB21L and cAB21H into the expression plasmid pcDNA3.1 respectively and transfer into *Escherichia coli* for amplification, and a large amount of expression plasmids with the gene encoding human-mouse chimeric antibodies (cAB21) were obtained.

Mixed the expression plasmids with cAB21 gene insertion with Fugen-6 liposome (Roche), and then co-transfected into CHO cells. Two to 3 days after cell transfection, collected the culture supernatants and added into 96-well plate pre-coated with human PD-1 protein, and use HRP enzyme labeled goat-anti-human-IgG (purchased from Shanghai Westang Bio-Tech Co., Ltd.) as the second antibody to detect the binding of collecting cAB21 supernatants to human PD-1 protein by ELISA.

Shown in Table 1 are the representative ELISA results.

TABLE 1

ELISA assay for the binding of supernatants from cells transiently transfected with cAB21 gene to human PD-1 protein

| supernatant dilution ratio | 1 | 2 | 4 | 8 | 16 | 32 | 64 | 128 |
|---|---|---|---|---|---|---|---|---|
| OD value at 492 nm | 1.699 | 1.075 | 0.685 | 0.433 | 0.334 | 0.297 | 0.230 | 0.217 |

The results in Table 1 show that supernatants from CHO cells transfected with cAB21 expression plasmids can specific bind to human PD-1 protein.

After loading the said supernatants from transfectd cells to Protein A-Sepharose Fast Flow (a product of GE), and centrifuging and 0.45-μm membrane filtration, human-mouse chimeric antibody (cAB21) proteins were obtained.

Example 8. Humanization Engineering of mAB21

Based on the fact that ELISA results showing cAB21 maintains the high-affinity binding to human PD-1 protein, then use PCR or other genetic-engineering cloning method, CDRs of either the light chain or the heavy chain of cAB21 were transplanted into the framework regions (FRs) of human kappa-light chain or the human IgG4-heavy-chain, respectively, thus the humanization version of this antibody, namely hAB21 was obtained.

1) Humanization of mAB21 Light Chain

Through the amino acid sequence analysis, it is determined that, the expression products of the germ-line gene in the first V region of the human immune globulin Kappa light-chain (IgKV1-9, NCBI Gene ID: 28941) and mAB21 light chain variable region share the highest homology. Accordingly, replaced the mAB21 light chain FRs with homologous sequences of the human IgKV1-9, and then fused the replaced variable region with the coding sequences of human IgG-Kappa light-chain constant region, the gene coding the humanized light chain (hAB21-L) was successfully obtained. See SEQ ID NO.: 11 for the amino acid sequence in the light chain variable region of hAB21, and SEQ ID NO: 13 for the nucleotide sequence thereof.

FIG. 6A is the comparative analysis of the amino acid sequence of hAb21 light-chain variable region with that of Nivolumab light-chain variable region as well as that of MK3475 light-chain variable region, with an "X" marked where the amino acid sequences in the light-chain variable region of hAb21 are different from those of Nivolumab or MK3475, and a box marked for the amino acid sequences of CDR1, CDR2 and CDR3 in the light-chain variable regions of each McAb. As shown in FIG. 6A, sequences in the light-chain variable region and CDRs of hAb21 are different from those of Nivolumab and MK3475.

2) Humanization of mAb21 Heavy-Chain

Through the amino acid sequence analysis, it is determined that, the expression products of the germ-line gene in the third V region of the human immune globulin Kappa heavy chain (IgHV3-23, NCBI Gene ID: 28442) and in mAB21 heavy chain variable region share the highest homology. Accordingly, replace the mAB21 heavy chain FRs with homologous sequences of the human IgHV3-23, and, meanwhile, fuse the genes encoding humanization mAB21 heavy chain variable region with the sequences in the constant region coding human immune globulin-IgG4 heavy chain, and replace serline, the original amino acid at the $228^{th}$ point location in the hinge region in the constant region of the IgG4 heavy chain with proline (S228P), for the purpose of reducing the lethal effect on PD-1 expressing positive immune cell (lymphocyte) by the antibody-dependent cellular cytotoxicity (ADCC) of the immune globulin-Fc receptor (FcR) binding and mediated in the humanization antibody and body. After a series of genetically engineering, a full-length humanization gene encoding hAB21 heavy chain variable chain and human IgG4-heavy chain constant region (S228P) was successfully obtained. See SEQ ID NO.: 12 for the amino acid sequence in the heavy chain variable region of hAB21, and SEQ ID NO: 14 for the nucleotide sequence thereof.

FIG. 6B is the comparative analysis of the amino acid sequence in hAb21 heavy-chain variable region with that of Nivolumab heavy-chain variable region, as well as that of MK3475 heavy-chain variable region, with an "X" marked where the amino acid sequence in the heavy-chain variable region of hAb21 is different from that of Nivolumab or MK3475, and a box region marked for the amino acid sequences of CDR1, CDR2 and CDR3 in the heavy-chain variable regions of each McAb. As shown in FIG. 6B, sequences in the heavy-chain variable region and CDRs of hAb21 are different from those of Nivolumab and MK3475.

Example 9. Establishment of Engineering CHO Cell Lines that Stably Secret and Express the Humanization Antibody hAb21, and Efficient Separation and Purification of Antibody Protein The humanized heavy-chain gene (hAB21H) and humanizedn light-chain gene (hAB21) were cloned into to the expression vector pcDNA3.1-Hygro step by step, and transferred into *Escherichia coli*. After amplification and purification, hAB21 expression plasmid were obtained. Afterwards, CHO cells were transiently transfected with the cAB21 and hAB21 gene expressing recombinant plasmids. Forty eight-hour after transfection, cell culture supernatants were collected and added into the plates coated with human PD-1 protein for detecting the binding of supernatant samples to PD-1 antigen by a direct ELISA method, HRP enzyme labeled goat-anti-human-IgG (purchased from Shanghai Westang Bio-Tech Co., Ltd.) was used as the second antibody for detection.

The following Table 2 shows the representative ELISA results.

TABLE 2

ELISA assay for the binding of supernatants from cells transiently transfected with cAB21 or hAB21 gene to human PD-1 protein b

| Dilutions of supernatants | OD value | |
|---|---|---|
| | cAB21 | hAB21 |
| 2 | 1.968 | 1.923 |
| 4 | 1.346 | 1.382 |
| 8 | 0.905 | 0.891 |
| 16 | 0.561 | 0.567 |
| 32 | 0.352 | 0.338 |
| 64 | 0.243 | 0.213 |
| 128 | 0.169 | 0.158 |
| 256 | 0.163 | 0.129 |

As shown in Table 2, humanized hAB21 antibodies (IgG4-kappa) maintain the binding to human PD-1 proteins, which is same as human-mouse cAB21 antibody.

A number of stably engineering CHO cell lines that efficiently secrete and express hAB21 proteins are successfully obtained. After sub-cloning, screening and cultured in-suspension in serum-free medium, these cell lines express the antibody at quantity over 1 g/L.

Afterwards, one engineering cell line was selected and amplified. After cultured in serum-free medium again and centrifugated, culture supernatants were collected and filtrated via 0.45 μm membrane. Supernatants were then subjected multiple steps of separation and purification processes, which includes a protein A-Sepharose Fast Flow (a product of GE), Ion-Exchange Column, virus removal and inactivation, sterile filtration (0.22 μm membrane filtration). Afterwards, a high purity (purity over 99%) hAB21 protein was finally obtained. The purified hAb21 protein was dissolved in physiological saline solution (1-20 mg/ml) and stored at below −20° C.

Example 10. ELISA Assay for the Binding of Purified hAb21 to FcR Protein

The binding of purified hAb21 (IgG4-kappa) to recombinant FcR receptor (such as FcγRI, CD64) protein coated on the 96-well plate can be detected by direct ELISA, and the results are compared with two other IgG4 type McAbs (Nivolumab and MK3475) and three IgG1 type McAbs (Avastin, hPV19 and Eribitux).

The basic procedures for this ELISA detection are as follows:

Add a serial diluted samples of IgG4 type McAbs (hAb21, Nivolumab and MK3475) or IgG1 type McAbs (Avastin, hPV19 and Eribitux) into the 96-well plate pre-coated with recombinant human FcγRI receptor proteins (CD64, a product from Sino Biological Inc.). After 2-hour incubation at 37° C. and washing, added HRP-labeled goat-anti-human-IgG-Fab (a product of Sigma) into each well. After another 1-hour incubation at 37° C. and washing, added the OPD substrate into each well for color development.

Figure 7:
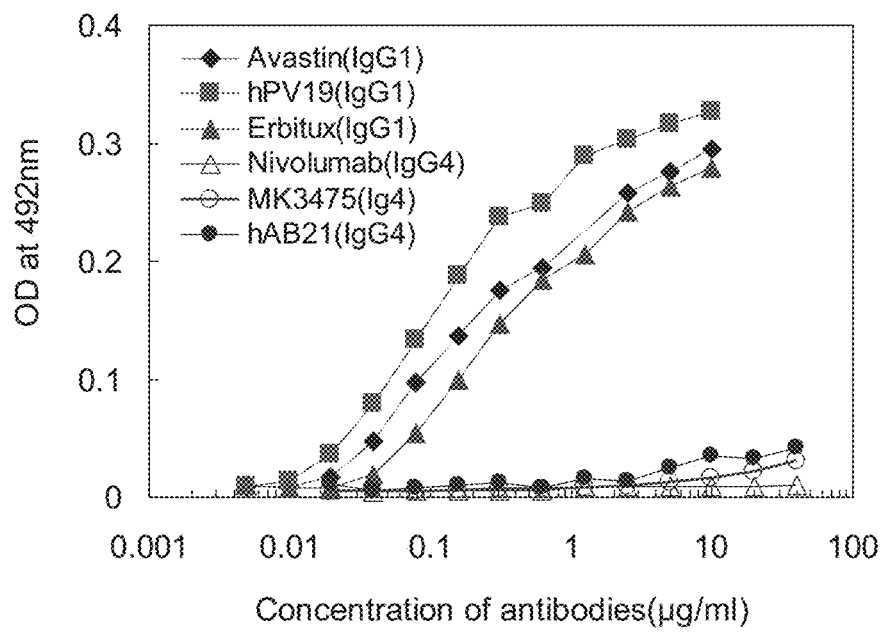
FIG. 7 is the diagrammatic drawing of a comparative analysis, showing the binding of three IgG4 McAbs (hAb21, Nivolumab, and MK3475) and three IgG1 McAbs (Avastin, hPV19 and Eribitux) to recombinant human FcR protein (CD64 protein) pre-coated on 96-well plates as described in example 10 of the invention.

FIG. 7 is the representative ELISA results. As shown in the Figure, compared with three IgG1 McAbs, (Avastin, hPV19 and Eribitux), the binding activity of three IgG4 McAbs (hAb21, Nivolumab and MK3475) to the FcγRI acceptor (CD64) is significantly reduced, which is in line with the forecast.

Example 11. ELISA Assay for the Binding of hAb21 to PD-1 and Other Immunity Related Proteins The binding of purified hAb21, Nivolumab and MK3475 to PD-1 protein and other related proteins can be detected by ELISA.

The basic procedures for the ELISA method are as follows:

Add a serial diluted samples of PD-1 McAbs (hAb21, Nivolumab and MK3475) or un-related hPV19 into 96-wells plate pre-coated with recombinant PD1-Fc or other immunity related gene-Fc fusion proteins (including CD28, B7, CTLA4, CD3, PD-L1, PD-L2, BTLA, etc). After 2-hour incubation at 37° C. and washing, added HRP-labeled goat-anti-human-IgG-Fab (a product of Sigma) into each well; after 1-hour incubation at 37° C. and washing, added the OPD substrate into each well for color development.

Figure 8:
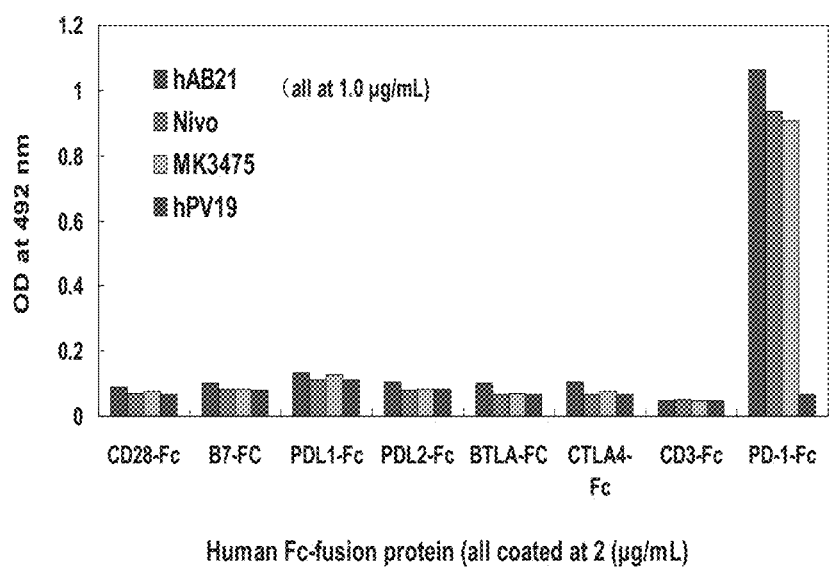
FIG. 8 is the diagrammatic drawing of ELISA results, comparative analysis of the binding of humanized hAb21, Nivolumab (Nivo) and MK3475 to human PD-1-Fc and other immune-related protein-Fc fusion proteins as described in example 11 of the invention. hPV19 is an irrelevant McAb sample, set as the negative control.

FIG. 8 is the representative ELISA results. As shown in the figure, similar to Nivolumab and MK3475, hAb21 only binds to human PD-1 protein and does not bind other immunity related proteins such as CD28, B7, CTLA4, CD3, PD-L1, PD-L2 and BTLA.

Example 12. Competitive ELISA Assay for Analysis the Binding Epitope of mAB21, Nivolumab and MK3475 to PD-1 Protein In order to determine whether the PD-1 binding epitope of Ab21 is different from that of Nivolumab or MK3475, the example compares and analyzes the PD-1 binding of mAB21, with that of Nivolumab and MK3475 in competitive ELISA manner, which is similar to the example 5.

Figure 9A:
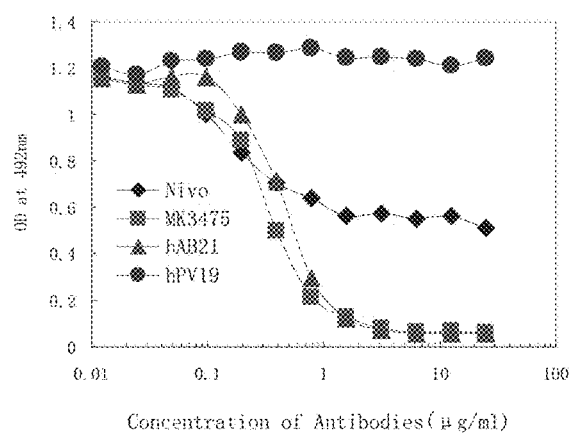
FIG. 9A is the diagrammatic drawing of in-vitro competitive ELISA results, showing the antagonizing and blocking of the binding of the biotin-MK3475 to the human PD-1 protein coated on a 96-well plate by humanized hAb21, Nivolumab (Nivo) and MK3475, as described in example 12 of the invention. hPV19 is an irrelevant McAb sample, set as the negative control.

FIG. 9A is the representative inhibiting results of hAb21, Nivolumab (Nivo) and MK3475 in antagonizing the binding of the biotin labelled MK3475 (biotin-MK3475) to human PD-1 proteins coated on 96-well plates, in the competitive ELISA assay. As shown in FIG. 9A, hAb21 has almost the same effect as MK3475 in antagonizing or inhibiting the binding of biotin-MK3475 to PD-1 proteins, and the inhibiting efficiency by Nivolumab is at about 50%, while the un-related McAb, hPV19 has no antagonistic action.

Figure 9B:
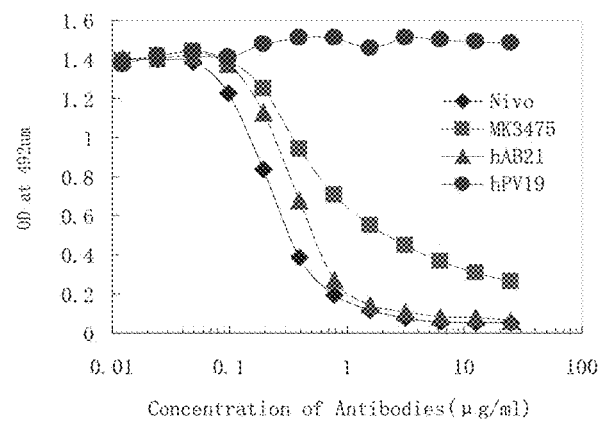
FIG. 9B is the diagrammatic drawing of in-vitro competitive ELISA results, showing the antagonizing and inhibiting of the binding of the biotin-Nivolumab to the human PD-1 protein coated on a 96-well plate by humanized hAb21, Nivolumab (Nivo) and MK3475, as described in example 12 of the invention. The hPV19 is an irrelevant McAb sample, set as negative control.

FIG. 9B is the representative inhibiting results of hAb21, Nivolumab (Nivo) and MK3475 in antagonizing the binding of the biotin labeled Nivolumab (biotin-Nivolumab) to human PD-1 proteins coated on 96-welle plates in the competitive ELISA assay. As shown in FIG. 9B, hAb21 has almost the same effect as Nivolumab in antagonizing or inhibiting the binding of biotin-Nivolumab to PD-1 proteins, and the inhibiting efficiency by MK3475 is about 70%, while the un-rrelated McAb hPV19 has no antagonistic action.

Figure 9C:
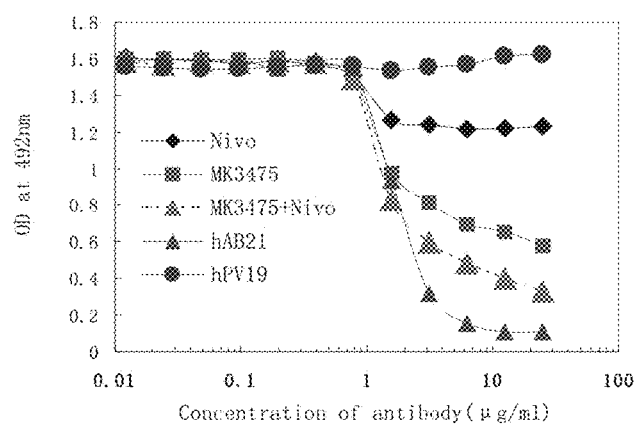
FIG. 9C is the diagrammatic drawing of in-vitro competitive ELISA results, showing the antagonizing and inhibiting of the binding of the botin-hAb21 to the human PD-1 protein coated on a 96-well plate by humanization hAb21, Nivolumab, MK3475, Nivolumab and MK3475+Nivo as described in example 12 of the invention. hPV19 is an irrelevant antibody.

FIG. 9C is the representative inhibiting results of hAb21, Nivolumab (Nivo), MK3475 and MK3475+Nivo in antagonizing the biotin labeled hAb21 (biotin-hAb21) to human PD-1 proteins coated on 96-well plates in the competitive assay. As shown in FIG. 9C, Nivolumab or MK3475 only partly antagonizes the binding of biotin-hAb21 to PD-1 proteins, seeing the antagonizing/inhibiting ratio of Nivolumab and MK3475 stay at about 20% and 50% respectively; moreover, the ratio of antagonizing and inhibiting the binding of biotin-hAb21 to PD-1 proteins may only reach about 70%, despite combination and simultaneous addition of Nivolumab and MK3475.

Upon comprehensive analysis of these competitive ELISA results, it can be said that the PD-1 protein binding epitope of hAb21 in this invention is significantly different from that of Nivolumab or MK3475.

Example 13. Flow-Cytometry (FCM) Analysis of the Binding of hAb21 or Nivolumab to CHO Cells Expressing Human PD-1 Gene (CHO/PD-1)

In the example, the binding of hAb21 or Nivolumab to CHO cells expressing human PD-1 gene is detected by flow-cytometry (FCM), with hAb21 or Nivolumab as the first antibody and FITC fluorescently-labeled goat-anti-human IgG as the second antibody.

For this purpose, CHO cells stably expressing human PD-1 gene (CHO/PD-1) were mixed normal CHO cells at the ration of 1:2, and then incubated with a solution containing different concentrations (0.003-10 μg/mL) of hAb21 or Nivolumab; after one-hour incubation at 4° C. and washing with PBS-0.1% FCS, added the FITC-labeled goat-anti-human IgG (a product of Sigma, 1:200 dilution) and incubated for an hour at 4° C.; after washing with PB S-0.1% FCS once more, the samples were subjected to flow-cytometry analysis (Cytomics FC500 MC, Beckman Coulter).

Figure 10A:
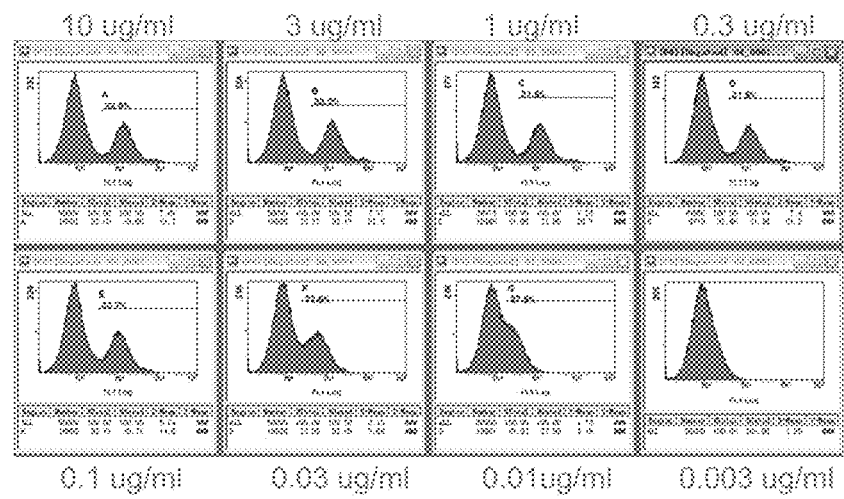
FIG. 10A is the diagrammatic drawing of FCM results, showing the binding of Nivolumab at different concentrations to CHO cells stably transfected with PD-1 gene as described in example 13 of the invention. The dot histograms are the IgG results, set as negative control.

FIG. 10A is the representative FCM results for Nivolumab. As shown in FIG. 10A, Nivolumab at 0.03-10 μg/mL concentrations can bind CHO/PD-1 cells, and the mean fluorescence intensity (MFI) of the binding is positively correlated with the concentrations of Nivolumab.

Figure 10B:
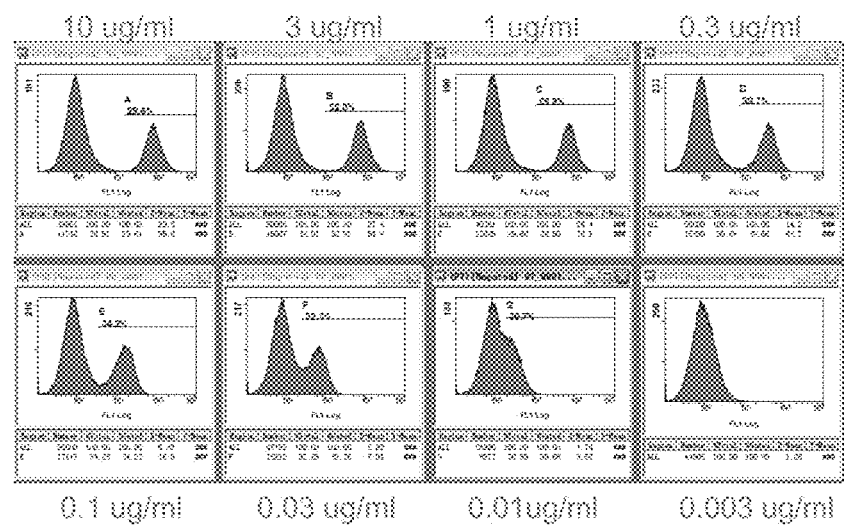
FIG. 10B is the diagrammatic drawing of the FCM results, showing the binding of mAB21 at different concentrations to CHO cells stably transfected with PD-1 gene as described in example 13 of the invention. The dot histograms are the IgG results, set as negative control.

FIG. 10B is the the representative FCM results for hAb21. As shown in FIG. 10B, hAb21 at 0.03-10 µg/mL concentrations can bind CHO/PD-1 cells, and the fluorescence intensity (MFI) of the binding is positively correlated with the concentrations of hAb21.

Figure 10C:
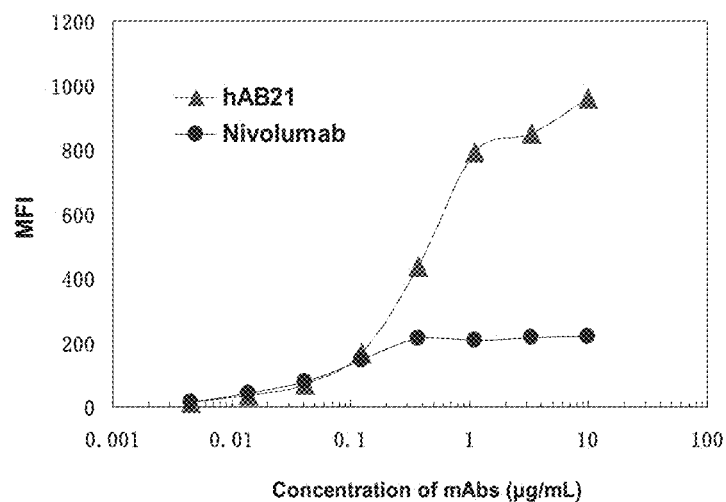
FIG. 10C is the dose-response curve showing the mean fluorescence intensity (MFI) and concentrations of hAb21 or Nivolumab as described in example 12 of the invention.

FIG. 10C is the mean fluorescence intensity (MFI) vs the concentration of hAb21 or Nivolumab curve. As shown in FIG. 10c, the binding fluorescence intensity of hAb21 to CHO-PD-1 cells is obviously stronger than that of Nivolumab.

Example 14. Flow-Cytometry (FCM) for the Analysis of the Binding of hAb21 or Nivolumab to Human-Jurkat T Cells Activated by PHA In the example, the binding of hAb21 or Nivolumab to human-Jurakt T cell line activated by PHA is detected by a flow-cytometry, with hAb21 or Nivolumab as the first antibody and FITC labeled goat-anti-human IgG as the second antibody.

For this purpose, human-Jurkat T cells (purchased from Cell Preservation Center of Shanghai Faculty of Life Sciences, CAS) were cultured with RPMI-10% FCS medium plus 3 µg/mL of phytohaemagglutinin PHA (Phytohaemagglutinin, a product of Sigma), which is a lymphocyte activating factor and can activate Jurkat T cells and inducing the expression of PD-1 proteins. 24 to 28 hours after PHA activation and induction, cells were centrifuged, separated and dissolved into solutions with different concentrations (0.1-3 µg/mL) of hAb21 or Nivolumab or with normal human-IgG (at 1 µg/mL) as the negative control. After one-hour incubation at 4° C. and washing with PBS-0.1% FCS, added FITC-labeled goat-anti-human IgG (a product of Sigma, 1:200); after one-hour incubation at 4° C. and washing with PBS-0.1% FCS fluids again, the samples were subjected to Cytomics FC500 MCL (a product of Beckman Coulter) for analysis.

Figure 11:
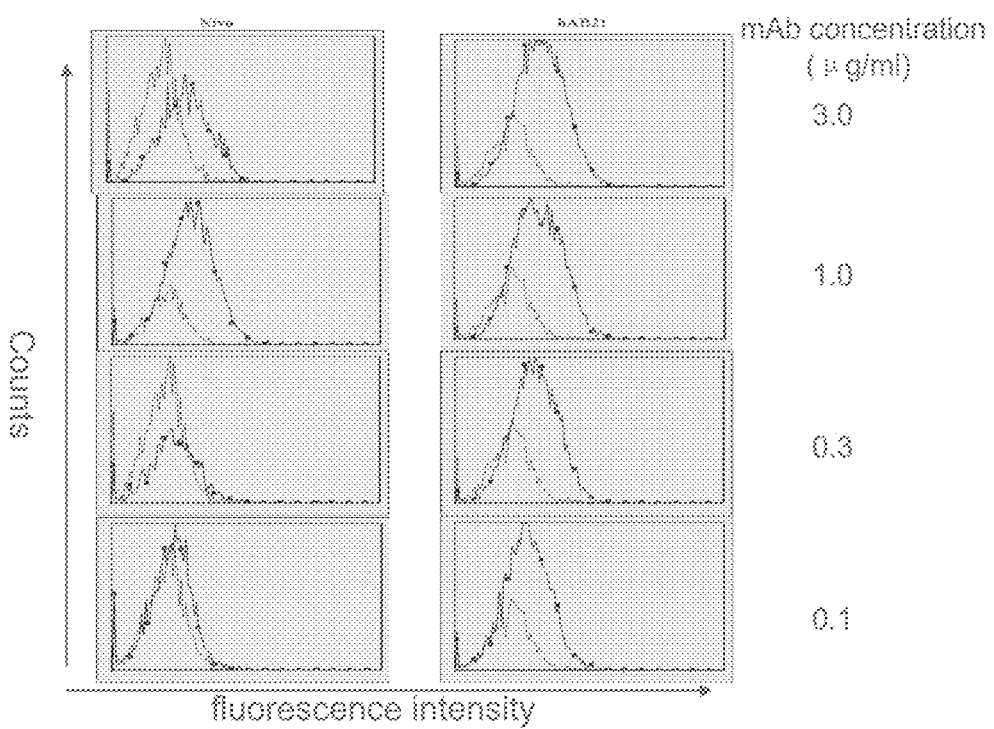
FIG. 11 is the diagrammatic drawing of FCM results, showing the binding of Nivolumab (Nivo, left) or hAb211 (hAb21, right) at different concentration to human Jurkat T cells activated by PHA in as described in example 14 of the invention. The dot histograms are the normal IgG results, set as negative control.

FIG. 11 is the FCM results of hAb21 (right) and Nivolumab (left). As shown in the figure, compared with the negative control IgG sample, both hAb21 and Nivolumab, at concentration of 1-3 µg/mL, bind PHA-activated Jurkat cells; hAb21 can still bind to Jurkat cells even at lower concentrations of 0.1-0.3 µg/mL, while the binding of Nivolumab to Jurkat cells is not significant.

Example 15. Flow-Cytometry (FCM) for Analysis of the Binding of hAb21 to Nivolumab and Human Peripheral Blood Mononuclear Cells (PBMCs) Activated by PHA In the example, the binding of hAb21 or Nivolumab to PHA-activated human peripheral blood mononuclear cells (PBMCs) was detected by flow-cytometry, with hAb21 or Nivolumab as the first antibody, and FITC fluorescently-labeled goat-anti-human IgG as the second antibody.

For this purpose, peripheral blood from healthy volunteers were loaded the into a definite volume of Ficol liquids, after centrifugation at normal temperature, the mononuclear cells were separated and then dissolved in RPMI-10% FCS culture medium with a phytohemagglutinin (PHA, a product of Sigma) at 3 µg/mL, which activates lymphocytes and induces the expression of PD-1 proteins. 48 to 72 hours after PHA activation and induction, the cells were centrifuged, separated and dissolved into solutions with different concentrations (0.015-4 µg/mL) of hAb21 or Nivolumab, or with the normal human-IgG samples (at 1 µg/mL) as the negative control. After one-hour incubation at 4° C. and washing with PBS-0.1% FCS, added the FITC-labeled goat-anti-human IgG (a product of Sigma, 1:200). After one-hour incubation at 4° C. and washing with PBS-0.1% FCS again, the samples were subjected to Cytomics FC500 MCL (Beckman Coulter) for analysis.

Figure 12:
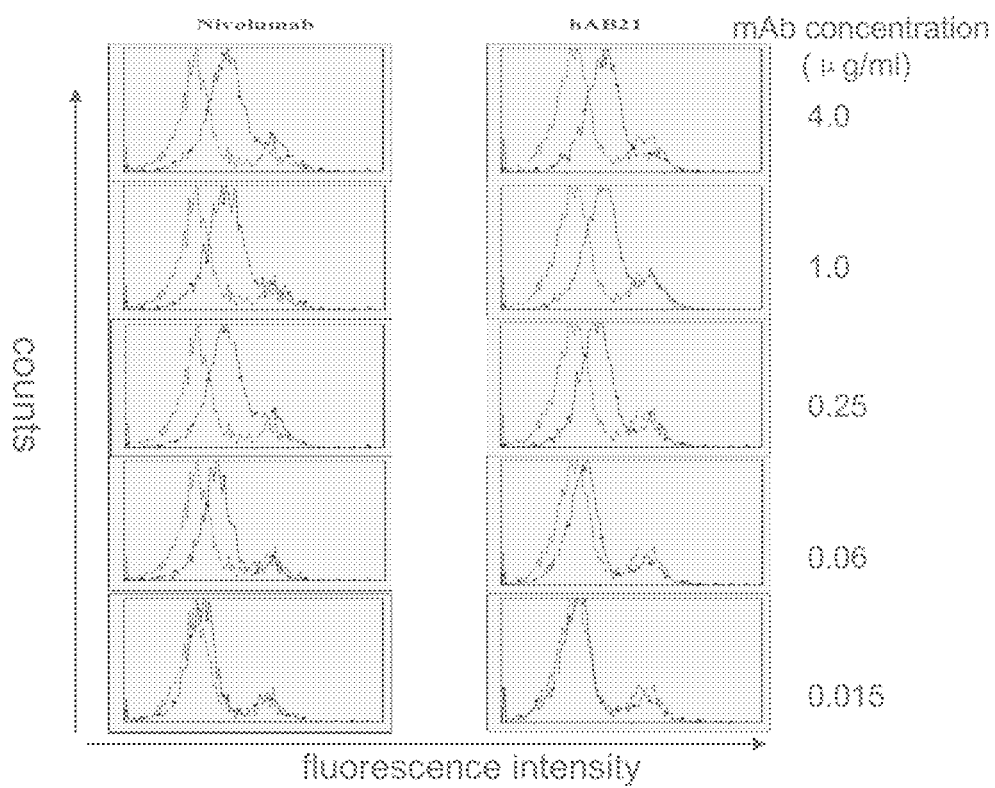
FIG. 12 is the diagrammatic drawing of FCM results, showing the binding of hAb21 (right) or Nivolumab (left) at different concentrations to hPBMC activated by PHA as as described in example 15 of the invention. The dot histograms are the normal IgG results, set as the negative control.

FIG. 12 is the FCM analysis results of hAb21 (right) and Nivolumab (left). As shown in FIG. 12, compared with the normal IgG sample (negative control), hAb21 and Nivolumab can bind PHA-activated human PBMC cells at concentrations of 0.25-4.0 µg/mL.

Example 16. Anti-Neoplastic Effect of hAb21 in PD-1 Humanization Mouse Model As hAb21 dose not recognize mouse PD-1, the effect of hAb21 cannot be tested directly in the normal mouse in-vivo. Hence, PD-1 humanization mice with a genetic engineering reconstruction were selected as the host for the in-vivo study of anti-neoplastic effect of hAb21 in the example.

This experimental study has two stages. Described in the following are the model, dosing, grouping and experimental results.

Study Stage 1:

Animal Model, Dosing and Grouping

Subcutaneously inoculate $1 \times 10^6$ mouse MC38 colon cancer cells, which was originate derived from C57BL/6 mice (provided by Souther China Animal-Model Inc.) at the right back of PD-1 humanization homozygote mice of C57BL/6 background (these PD-1 humanization mice, by replacing the mouse PD-1 gene with the human PD-1 gene through homologous gene recombination, express human PD-1 rather than mouse endogenous PD-1 protein); when the inoculated tumor volume reached the size of a rice grain (about 40-50 mm$^3$, 6 to 7 days after tumor cell inoculation), randomly divide the animals into 3 different treatment groups as follows:

Group A: treatment with normal saline (NS) negative control (n=6, same volume of saline)

Group B: treatment with pembrolizumab (MK3475) (n=6, administration dose: 10 mg/kg)

Group C: treatment with hAb21 (n=6, administration dose: 10 mg/kg)

Animals were administered through intraperitoneal injection (i.p.) twice a week (every other 3 to 4 days), for 4 times successively, 2 weeks in total for dosage, from the same day of grouping the animals, i.e. on the sixth to seventh day after tumor inoculation. During the treatment period, animals were observed for the general clinical symptoms every day and the major axis (mm) and minor axis (mm) of the tumor and weight of animals were measured every other 3 to 4 days. Computational formula of the tumor volume is Volume (mm$^3$)=Major Axis (mm)×Minor Axis (mm)×Minor Axis (mm)×0.5. The animals are euthanized if the tumor volume reaches over 4000 mm$^3$ when measuring.

Figure 13A:
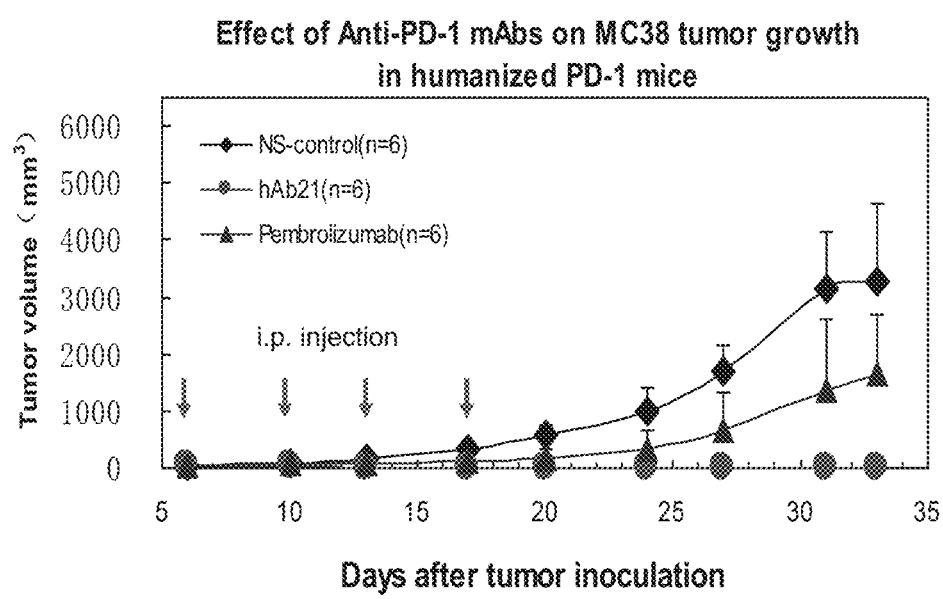
FIG. 13A is the growth curve of murine MC38 colon cancer cells under the skin of PD-1 humanized mice in example 16 of the invention after the administration of hAb21 or MK3475 (Pembrolizumab) in the study stage 1.

Animal Treatment Results:

FIG. 13A shows the increment trend of the average tumor volume in testing animals in each group.

Figure 13B:
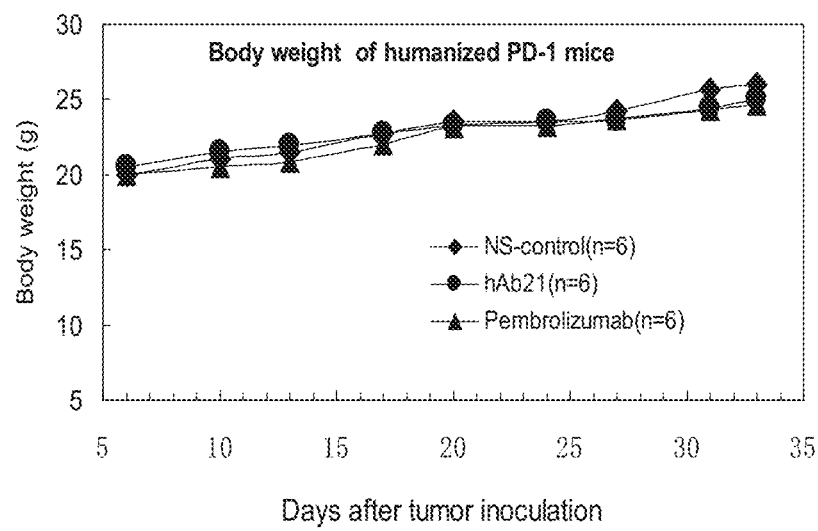
FIG. 13B is the growth curve of mouse weight after administration of hAb21 or MK3475 (Pembrolizumab) in the study stage 1. Murine MC38 colon cancer cells were inoculated under the skin of PD-1 humanization mice in example 16 of the invention.

FIG. 13B shows the trend of the average weight growth of testing animals in each group.

Figure 14A:
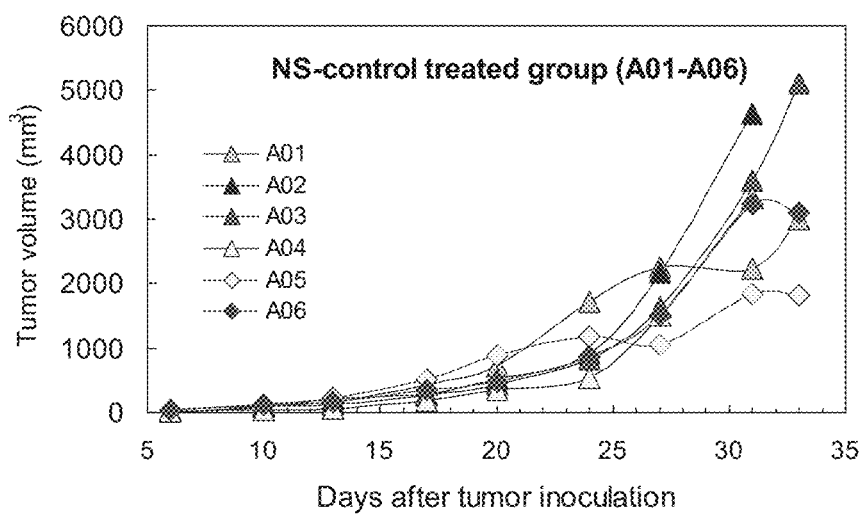
FIG. 14A shows the tumor growth volume trend in each individual animal from normal saline (NS)-treated negative control group (Group A) in the study stage 1. Murine MC38 colon cancer cells were inoculated under the skin of PD-1 humanized mice in example 16 of the invention.
Figure 14B:
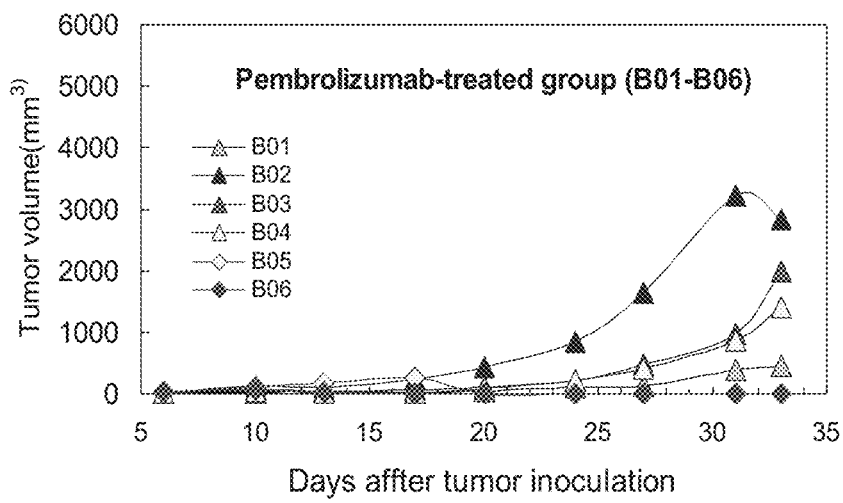
FIG. 14B shows the tumor growth volume trend in every individual animal in the McAb Pembrolizumab (MK3475) treatment group (Group B) in the study stage 1. Murine MC38 colon cancer cells were inoculated under the skin of PD-1 humanization mice in example 16 of the invention.
Figure 14C:
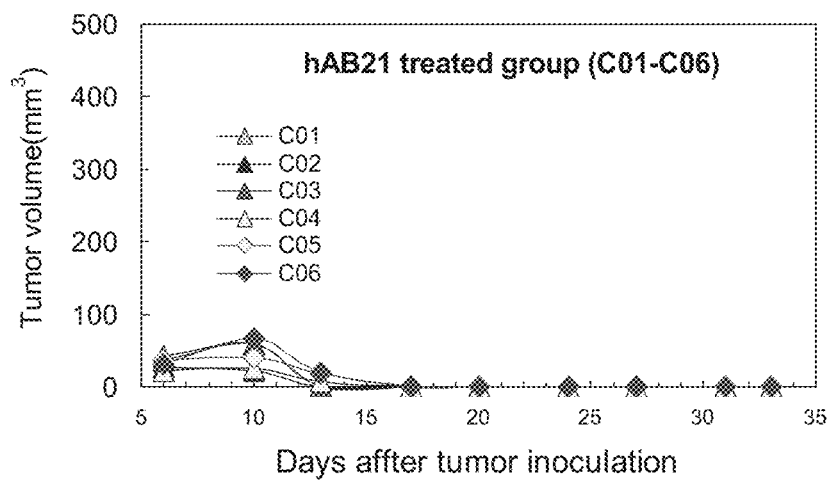
FIG. 14C shows the tumor growth volume trend in each individual animal in McAb hAb21 treatment group (C) (Group A) in the study stage 1. Murine MC38 colon cancer cells were inoculated under the skin of PD-1 humanization mice in example 16 of the invention.

FIG. 14A, FIG. 14B and FIG. 14C show the increment trend of the tumor volume of each individual animal in each treatment group.

The following Table 3-5 show the results of the tumor growth volume in every animal from each treatment group.

TABLE 3

Tumor Volume (mm³) in Mice Treated With NS-control group (n = 6)

| Day (*) | A01 Male | A02 Male | A03 Male | A04 Male | A05 Female | A06 Female | X ± SD |
|---|---|---|---|---|---|---|---|
| 6 (1) | 41.43 | 0.00 | 38.44 | 12.41 | 48.09 | 42.49 | 36.57 ± 13.95 |
| 10 (5) | 1.18.61 | 77.18 | 101.82 | 51.47 | 120.54 | 118.38 | 98.00 ± 28.15 |
| 13 (8) | 160.43 | 215.27 | 133.71 | 57.95 | 221.13 | 171.34 | 159.97 ± 60.04 |
| 17 (12) | 424.24 | 289.95 | 259.86 | 184.88 | 517.78 | 348.34 | 337.51 ± 119.77 |
| 20 (15) | 721.57 | 512.14 | 436.79 | 342.49 | 884.80 | 467.41 | 560.87 ± 202.46 |
| 24 (19) | 1713.94 | 917.43 | 820.05 | 534.34 | 1172.97 | 860.01 | 1003.12 ± 403.78 |
| 27 (22) | 2247.93 | 2181.73 | 1632.56 | 1502.21 | 1064.69 | 1507.39 | 1689.42 ± 450.78 |
| 31 (26) | 2231.64 | 4633.67 | 3604.40 | 3323.73 | 1831.16 | 3228.38 | 3142.17 ± 1002.64 |
| 33 (28) | 3008.70 | euthanized | 5114.15 | died | 1815.58 | 3111.68 | 3262.53 ± 1367.40 |
| 36 (30) | 4012.72 | — | euthanized | — | 1649.23 | 4503.91 | 5031.74 ± 2773.09 |
| 41 (35) | euthanized | — | — | — | 3680.48 | euthanized | |
| 43 (37) | — | — | — | — | 3978.30 | — | |
| 47 (4l) | — | — | — | — | 4099.00 | — | |
| 50 (44) | — | — | — | — | euthanized | — | |

*: Numbers in ( ) are days after received 1st treatment

TABLE 4

Tumor Volume (mm³) in Mice Treated with Pembrolizumab (n = 6)

| Day (*) | B01 Male | B02 Male | B03 Male | B04 Male | B05 Female | B06 Female | X ± SD |
|---|---|---|---|---|---|---|---|
| 6 (1) | 30.56 | 22.79 | 29.32 | 24.18 | 30.70 | 41.16 | 29.78 ± 6.50 |
| 10 (5) | 23.33 | 128.52 | 63.63 | 47.67 | 103.59 | 70.55 | 72.88 ± 38.00 |
| 13 (8) | 51.16 | 105.06 | 41.73 | 23.81 | 167.18 | 23.80 | 68.79 ± 56.72 |
| 17 (12) | 22.77 | 241.38 | 59.74 | 26.19 | 255.82 | 0.00 | 121.18 ± 117.32 |
| 20 (15) | 50.06 | 430.81 | 113.29 | 84.15 | died | 0.00 | 169.58 ± 176.06 |
| 24 (19) | 107.61 | 840.71 | 218.00 | 223.65 | — | 0.00 | 347.49 ± 333.12 |
| 27 (22) | 136.26 | 1642.37 | 485.24 | 414.80 | — | 0.00 | 669.67 ± 665.74 |
| 31 (26) | 381.32 | 3217.38 | 982.94 | 871.32 | — | 0.00 | 1363.24 ± 1263.41 |
| 33 (28) | 452.82 | 2831.28 | 1991.67 | 1403.44 | — | 0.00 | 1669.80 ± 1000.17 |
| 36 (30) | 970.64 | 4294.38 | 2153.35 | 1903.74 | — | 0.00 | 2330.53 ± 1404.70 |
| 41 (35) | 2296.81 | died | 6356.19 | 4431.87 | — | 0.00 | 4361.62 ± 2030.60 |
| 43 (37) | 8852.36 | — | died | euthanized | — | 0.00 | |
| 47 (41) | euthanized | — | — | — | — | 0.00 | |
| 50 (44) | euthanized | — | — | — | — | 0.00 | |

*: Numbers in ( ) are days after received 1st treatment

TABLE 5

Tumor Volume (mm³) in Mice Treated with hAb21 mAb (n = 6)

| Day (*) | C01 Male | C02 Male | C03 Male | C04 Male | C05 Female | C06 Female | X ± SD |
|---|---|---|---|---|---|---|---|
| 6 (1) | 42.19 | 28.25 | 36.29 | 21.62 | 36.80 | 31.52 | 32.78 ± 7.26 |
| 10 (5) | 58.82 | 21.18 | 58.63 | 25.74 | 40.78 | 66.18 | 45.22 ± 18.87 |
| 13 (8) | 0.00 | 0.00 | 0.00 | 8.10 | 17.85 | 20.89 | 15.61 ± 6.68 |
| 17 (12) | 0.00 | 0.00 | 0.00 | 0.00 | 0.00 | 0.00 | 0.00 ± 0.00 |
| 20 (15) | 0.00 | 0.00 | 0.00 | 0.00 | 0.00 | 0.00 | 0.00 ± 0.00 |
| 24 (19) | 0.00 | 0.00 | 0.00 | 0.00 | 0.00 | 0.00 | 0.00 ± 0.00 |
| 27 (22) | 0.00 | 0.00 | 0.00 | 0.00 | 0.00 | 0.00 | 0.00 ± 0.00 |
| 31 (26) | 0.00 | 0.00 | 0.00 | 0.00 | 0.00 | 0.00 | 0.00 ± 0.00 |
| 33 (28) | 0.00 | 0.00 | 0.00 | 0.00 | 0.00 | 0.00 | 0.00 ± 0.00 |
| 36 (30) | 0.00 | 0.00 | 0.00 | 0.00 | 0.00 | 0.00 | 0.00 ± 0.00 |
| 41 (35) | 0.00 | 0.00 | 0.00 | 0.00 | 0.00 | 0.00 | 0.00 ± 0.00 |
| 43 (37) | 0.00 | 0.00 | 0.00 | 0.00 | 0.00 | 0.00 | 0.00 ± 0.00 |
| 47 (41) | 0.00 | 0.00 | 0.00 | 0.00 | 0.00 | 0.00 | 0.00 ± 0.00 |
| 50 (44) | 0.00 | 0.00 | 0.00 | 0.00 | 0.00 | 0.00 | 0.00 ± 0.00 |

*: Numbers in ( ) are days after received 1st treatment

As shown in Table 3-5, FIG. 13A, FIG. 14A, FIG. 14B and FIG. 14C, compared with the negative control NS-treatment group, tumor growth in hAb21 or Pembrolizumab treatment group is inhibited at 5 to 8 days after the starting of the treatment.

More surprising and encouraging is that the treatment effect of hAb21 is much better than of Pembrolizumab. In hAb21 treatment group, after dosage for two times or on the 8th day after first dosage, transplanted tumors appeared atrophy or totally disappear in all the tested animals (6/6); tumors do not re-grow even after ceases of the treatment after dosage for 4 times (the last dosage), the test has been observed for 50 days after the tumor inoculation, i.e, on the 32nd day after the last dosage). In Pembrolizumab treatment group treated, only one animal (⅙) showed tumor atrophy or disappear after dosage for three times, i.e. on the 12th day after the first dosage, and in other animals tumors all re-grow after 4-time dosing treatment (and one animal is found dead on the 15th day after the first dosage), and the remaining 4 animals were dead or have to be euthanized on the 43rd day after the tumor inoculation.

FIG. 13B shows the average weight growth trend of treated animals in each group. As shown in FIG. 13B, compared with the NS negative control group, of hAb21 or Pembrolizumab treatment have no influence on the weight-gain of the treated animals.

Study Stage 2 Study Objective, Animal Model and Treatment Group

Stage 2 of the study is to assess whether the previous hAB21 treated PD-1 humanization mice would be able to reject re-inoculated MC38 tumor without continuous administration (preliminary verification of the immunologic memory function).

Animal Experimental Model and Grouping

The treatment has two groups:

Treatment group C: About 20 days after tumor being rejected (i.e. the $10^{th}$ day after the last dosing of hAB21 mAb), subcutaneously re-inoculate $1\times10^6$ MC38 tumor cells on the other side (left) of those 6 PD-1 humanization mice that have previously received hAB21 treatment and completely rejected MC38 tumors.

Control group D: Inoculate $1\times10^6$ MC38 tumor cells in the skin on the left side of 5 wild-type C57BL/6 mice (6 to 8 weeks old)

Animals in these two groups receive no treatment during the study. Then observe the general clinical symptoms of animals every day from the $6^{th}$ day after tumor inoculation and measure the major axis (mm) and minor axis (mm) of tumor and weight of animals every other 3 to 4 days. The computational formula of the tumor volume is Volume $(mm^3)$=Major Axis (mm)×Minor Axis (mm)×Minor Axis (mm)×0.5.

Figure 15:
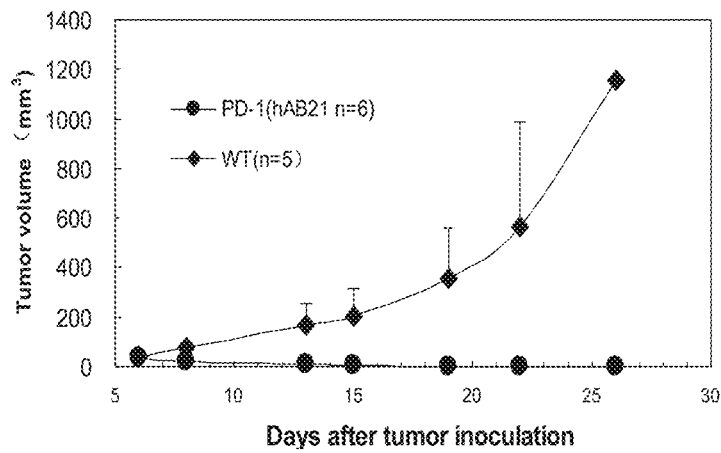
FIG. 15 is a comparison of the growth chart of re-inoculated tumors with that of inoculated under the skin of C57BL/6 wild-type mice, in the study stage 2. Murine MC38 colon cancer cells were inoculated under the skin of PD-1 humanization mice in example 16 of the invention.

Animal Treatment Results:

FIG. 15 shows the increment trend of the average tumor volume in tested animals in each group.

The following Table 6 is the measuring results of the tumor growth volume in each individual animal from each group.

Example 17. Anti-Neoplastic Activity of hAb21 Tested in Normal, C57ML/6 Wild-Type Mice Study Objective:

The objective of the study is to assess whether hAB21 treatment will reject tumor in normal, wild-type mice which do not express human PD-1 gene.

Animal Experimental Model and Grouping:

Subcutaneously inoculate $1\times10^6$ MC38 tumor cells into normal, C57BL/6 wild-type mice (6 to 8 weeks old), when the volume of inoculated tumors reaching the size of a rice grain (about 40-50 $mm^3$, on the $6^{th}$ day or so after the tumor cell inoculation), randomly divide the animals into 2 groups as the follows:

Group A: NS negative control treatment (n=6, equal volume of normal saline)

Group B: hAb21 treatment group (n=6, administration dose: 10 mg/kg)

Starting at the same day of grouping the animals (i.e., on the $6^{th}$ day after tumor inoculation), administer animals through intraperitoneal injection (i.p.) twice every week (every other 3 to 4 days), for 4 times, 2 weeks in total for administer dosage.

During the treatment period, observe the general clinical symptoms of animals every day and measure the major axis (mm) and minor axis (mm) of tumor and weight animals every other 3 to 4 days.

TABLE 6

MC38 Tumor Growth Volume ($mm^3$) in Wild-type C57BL/6 Mice or in Humanized PD-1 Mice have been previously Treated with hAb21 mAb

| Group C: Humanized PD-1 Mice have been treated with hAb21 mAb (n = 6) | | | | | | | |
|---|---|---|---|---|---|---|---|
| Day (*) | C01 Male | C02 Male | C03 Male | C04 Male | C05 Female | A06 Female | X ± SD |
| 6 (36) | 41.52 | 4.96 | 4.00 | 0.00 | 123.66 | 51.68 | 37.64 ± 47.39 |
| 8 (38) | 4.90 | 0.50 | 0.00 | 0.00 | 66.32 | 60.67 | 22.07 ± 32.20 |
| 13 (43) | 0.00 | 0.00 | 0.00 | 0.00 | 55.05 | 8.94 | 10.66 ± 22.04 |
| 15 (55) | 0.00 | 0.00 | 0.00 | 0.00 | 36.34 | 0.00 | 6.06 ± 14.84 |
| 19 (49) | 0.00 | 0.00 | 0.00 | 0.00 | 0.00 | 0.00 | 0.00 ± 0.00 |
| 22 (52) | 0.00 | 0.00 | 0.00 | 0.00 | 0.00 | 0.00 | 0.00 ± 0.00 |
| 26 (56) | 0.00 | 0.00 | 0.00 | 0.00 | 0.00 | 0.00 | 0.00 ± 0.00 |

| Group D: Wild-type C57BL/6 Mice (n = 5) | | | | | |
|---|---|---|---|---|---|
| Day | D01 Female | D02 Female | D03 Female | D04 Female | D05 Female | X ± SD |
| 6 | 53.42 | 48.68 | 60.62 | 36.92 | 16.28 | 43.18 ± 17.33 |
| 8 | 69.39 | 95.23 | 80.78 | 38.65 | 90.40 | 74.89 ± 22.54 |
| 13 | 199.95 | 283.99 | 186.53 | 47.24 | 112.44 | 166.03 ± 90.09 |
| 15 | 231.42 | 356.01 | 235.80 | 52.27 | 149.21 | 204.94 ± 112.80 |
| 19 | 405.98 | 588.07 | 481.48 | 80.93 | 222.19 | 355.73 ± 203.51 |
| 22 | 543.46 | 1204.30 | 693.60 | 143.40 | 247.52 | 566.46 ± 419.60 |
| 26 | 1414.89 | 2142.11 | 1290.40 | 328.72 | 613.29 | 1157.88 ± 713.51 |

●: Numbers in ( ) are days after $1^{st}$ inoculation of MC38 tumor in humanized PD-1 mice As shown in Table 6 and FIG. 15, MC38 tumors inoculated in the C57BL/6 wild-type mice grow rapidly, while the re-inoculated MC38 tumors in those PD-1 humanization mice previously treated with hAb21 do not grow during the observation period or are totally rejected starting from at $8^{th}$ to $15^{th}$ day after the tumor inoculation. These preliminary results show that PD-1 humanization mice, after being successfully treated with hAB21, do have immunological memory and are able to reject re-inoculated MC38 tumors without any new treatment.

The computational formula of the tumor volume is Volume $(mm^3)$=Major Axis (mm)×Minor Axis (mm)×Minor Axis (mm)×0.5. The treated animals will be euthanized in case of the tumor volume over 4000 $mm^3$ when measuring.

Figure 16:
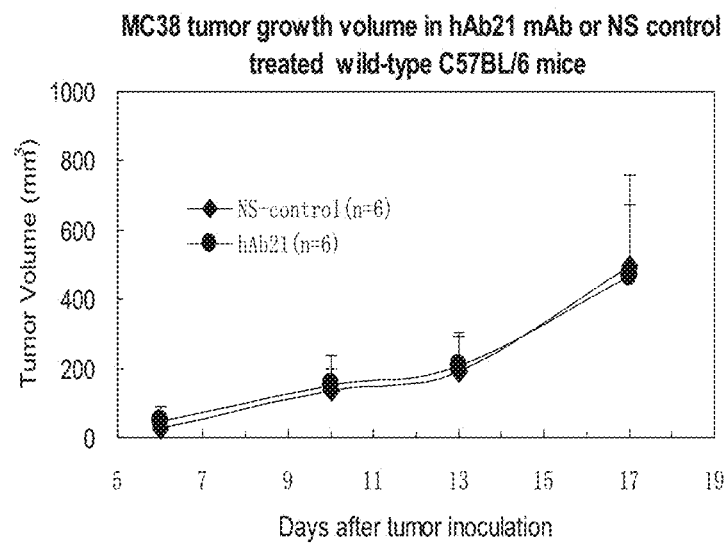
FIG. 16 shows the tumor growth volume trend in animals treated with hAb21 or NS control. Murine MC38 colon cancer cells were inoculated under the skin of C57BL/6 wild-type mice in example 17 of the invention.

Treatment Results:

FIG. 16 shows the increment trend of the average tumor volume in treated animals from these two groups.

Table 7 is the measuring result of tumor growth volume in individual animals from each group.

TABLE 7

MC38 Tumor Growth Volume (mm³) in C57BL/6 WT Mice

Group A: WT Mice treated with NS-control (n = 6)

| Day (*) | A01 Male | A02 Male | A03 Male | A04 Male | A05 Female | A06 Female | X ± SD |
|---|---|---|---|---|---|---|---|
| 6 (1)   | 33.36  | 20.22  | 52.24  | 57.48  | 4.00   | 4.00   | 28.55 ± 23.22 |
| 10 (5)  | 99.91  | 128.04 | 127.58 | 158.06 | 56.73  | 241.41 | 135.29 ± 62.15 |
| 13 (8)  | 138.56 | 131.20 | 151.95 | 357.05 | 100.33 | 267.11 | 191.03 ± 99.44 |
| 17 (12) | 336.01 | 355.12 | 441.55 | 829.60 | 193.00 | 807.96 | 493.87 ± 264.12 |

Group B: WT Mice treated with hAb21 mAb (n = 6)

| Day (*) | B01 Male | B02 Male | B03 Male | B04 Male | B05 Female | B06 Female | X ± SD |
|---|---|---|---|---|---|---|---|
| 6 (1)   | 98.18  | 93.25  | 49.80  | 36.65  | 0.00   | 0.00   | 46.31 ± 43.10 |
| 10 (5)  | 286.47 | 205.51 | 114.13 | 147.57 | 44.74  | 113.91 | 152.05 ± 84.09 |
| 13 (8)  | 383.45 | 216.66 | 178.88 | 204.04 | 95.37  | 152.77 | 205.20 ± 97.38 |
| 17 (12) | 833.31 | 392.57 | 389.95 | 390.62 | 229.95 | 559.44 | 465.98 ± 207.95 |

*: Numbers in ( ) are days after received 1st treatment

As shown in the above Table 7 and FIG. 16 above, the growth volume trend of MC38 tumors in hAb21 treated group is essentially identical to that in NS-treated control group. These results show that hAB21 has no obvious effect on tumor growth in the normal, wild-type mice which do not express human PD-1 gene.

Example 18. Experimental Evaluation on the Preliminary Drug Metabolism and Toxicology/Safety hAb21 in Monkeys As it is known that mAB21 can recognize and bind monkey PD-1 (see example 3), the normal monkeys are selected as the testing hosts to preliminary assess the pharmacokinetics and toxicology/safety of hAb21 when infused intravenously. These experiments in this example were performed by JOINN Laboratories (Suzhou).

Two male monkeys were selected for this experiment and each received a single injection of hAB21 at a dosage of 10 mg/kg body-weight. After this injection, collected sera at different time-points, and the amount of hAB21 in serum samples were detected by a proven ELISA method. During the experiment period, these two animals showed no abnormality in mental behavior or activity after received a single fusio of hAB21 injection at the dose of 10 mg/kg.

The major pharmacokinetics parameters of hAB21 in each animal after dosage are calculatede by using WinNonlin.

TABLE 8

Pharmacokinetics parameters of hAb21 after a single intravenous infusion in monkeys

| Animal Dosing group | Animal No. | $t_{1/2}$* (h) | Tmax (h) | Cmax (μg/mL) | $AUC_{last}$ (h·mg/mL) | $AUC_{inf}$ (h·mg/mL) |
|---|---|---|---|---|---|---|
| mAB21 (10 mg/kg) | 1 | 402.56 | 8.00 | 234.06 | 55.25 | 76.81 |
|                  | 2 | 58.84  | 4.00 | 247.22 | 37.98 | 38.08 |

Figure 17:
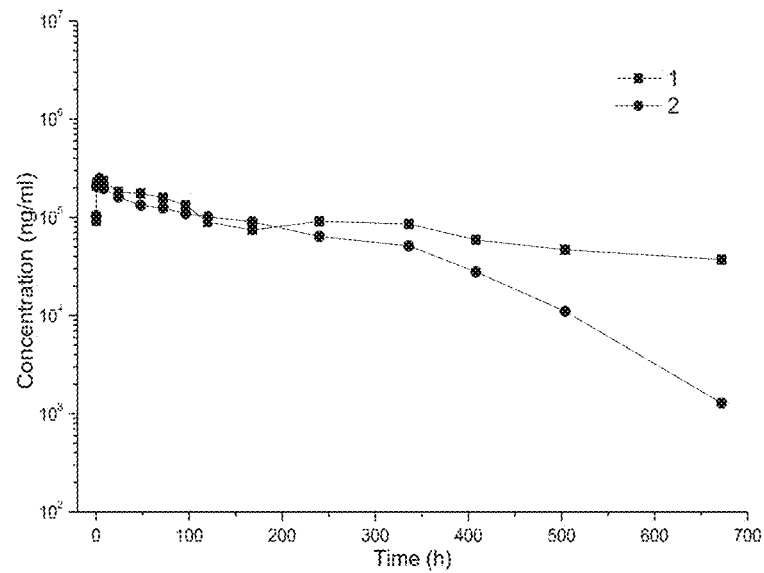
FIG. 17 is a drug concentration-time profile of hAB21 after a single intravenous injection in monkeys in example 18 of the invention.

*means that the animal may generate the drug resistant antibody which influences the blood concentration detection As shown in Table 8 and FIG. 17, after the intravenous infusion of hAB21 at a dose of 10 mg/kg, the Cmax of hAB21 in these two monkeys is very similar, which are 234.06 μg/mL and 247.22 m/mL respectively; the tv2 is 402.56 h and 58.84 h respectively. The blood concentration of hAB21 declines sharply on the 28th day after the injection in animal No. 2, and it is suspected that this animal may have generated anti-drug antibodies around day 17 day after the injection, which would influence the pharmacokinetics parameters of hAB21 such as tv2.

As the amino acid sequences of human immuneglobulins are different from those of immuneglobulins of non-human primates (such as monkeys), it is not surprising that after adminstration of immunogenic human or humanization antibody drugs into monkeys, anti-drug antibodies (anti-antibody antibodies) are generated (vanMeer P J, et al. Immunogenicity of mabs in non-human primates during nonclinical safety assessment. MAbs 2013; 5:810-6). In-fact, during the BMS's non-clinical study of its fully-human mAb Nivolumab in non-human primate (monkeys), it was also found that anti-Nivolumab antibodies (including neutralizing antibodies) were detected on the 28th day after dosage, in 5 out of 6 animals from 1 mg/kg dosage group and 2 out of 3 animals from 10 mg/kg dosage group. However, the occurrence of anti-antibody antibodies has no adverse effect on the testing animals (Wang C et al: Cancer Immunol Res. 2014; 2: 1-11).

What is claimed is:

1. A monoclonal antibody antagonizing and inhibiting the binding of human PD-1 antigen to a ligand of the human PD-1 antigen, comprising: a first variable region and a second variable region, wherein the first variable region is an antibody light chain variable region having a first complementarity-determining region 1 (CDR1) with the amino acid sequence of SEQ ID NO: 3, a first complementarity-determining region 2 (CDR2) with the amino acid sequence of SEQ ID NO: 4, and a first complementarity-determining region 3 (CDR3) with the amino acid sequence of SEQ ID NO: 5, and the second variable region is an antibody heavy chain variable region having a second CDR1 with the amino acid sequence of SEQ ID NO: 8, a second CDR2 with the amino acid sequence of SEQ ID NO:9, and a second CDR3 with the amino acid sequence of SEQ ID NO: 10.

2. The monoclonal antibody according to claim 1, wherein, the first variable region is an antibody light chain variable region having the amino acid sequence of SEQ ID NO: 11, and the second variable region is an antibody heavy chain variable region having the amino acid sequence of SEQ ID NO: 12.

3. The monoclonal antibody according to claim 1, further comprising a human antibody light chain constant region, and a hinge region including the antibody heavy chain variable region and a human antibody heavy chain constant region, wherein the human antibody heavy chain constant region includes a constant heavy region 1 (CH1), a constant heavy region 2 (CH2) and a constant heavy region 3 (CH3).

4. The monoclonal antibody according to claim 3, wherein, the human antibody light chain constant region is from a human antibody kappa chain or a human antibody lamda chain, and the human antibody heavy constant region is from a human subtype IgG1, IgG2, IgG3 or IgG4.

5. A DNA molecular sequence encoding the monoclonal antibody according to claim 2, comprising: a nucleotide sequence of the antibody light chain variable region shown in SEQ ID NO: 13, and a nucleotide sequence of the antibody heavy chain variable region shown in SEQ ID NO: 14.

6. An expression vector, comprising: the DNA molecular sequence of claim 5, and an expression regulation sequence operably linked to the DNA molecule.

7. A reconstitution host cell, formed by transforming with the expression vector of claim 6.

8. A daughter cell of the reconstitution host cell according to claim 7, expressing a monoclonal antibody antagonizing and inhibiting the binding of human PD-1 antigen to a ligand of the human PD-1 antigen, wherein the monoclonal antibody comprises a first variable region and a second variable region, wherein the first variable region is an antibody light chain variable region having a first complementarity-determining region 1 (CDR1) with the amino acid sequence of SEQ ID NO: 3, a first complementarity-determining region 2 (CDR2) with the amino acid sequence of SEQ ID NO: 4, and a first complementarity-determining region 3 (CDR3) with the amino acid sequence of SEQ ID NO: 5, and the second variable region is an antibody heavy chain variable region having a second CDR1 with the amino acid sequence of SEQ ID NO: 8, a second CDR2 with the amino acid sequence of SEQ ID NO:9, and a second CDR3 with the amino acid sequence of SEQ ID NO: 10.

9. A medicine comprising a pharmaceutically effective amount of the monoclonal antibody of claim 1 and a pharmaceutically acceptable carrier.

10. A method of using the medicine according to claim 9 in preparing agents for cancer treatment, comprising: using the medicine in preparing the agents for cancer treatment.

11. The method according to claim 10, wherein the cancer is colon cancer.

12. A method for preparing the monoclonal antibody according to claim 1, comprising the following steps:
  a) providing an expression vector containing a DNA molecular sequence and an expression regulation sequence, wherein the DNA molecular sequence comprises a nucleotide sequence of the antibody light chain variable region shown in SEQ ID NO: 13, and a nucleotide sequence of the antibody heavy chain variable region shown in SEQ ID NO: 14;
  b) transforming host cells with the expression vector set forth in the step a) to obtain transformed host cells;

c) culturing the transformed host cells got from the step b) in a host cell culture fluid under conditions suitable for an expression of the monoclonal antibody; and
d) getting the monoclonal antibody by the separation and purification of the host cell culture fluid with affinity chromatography.

13. The monoclonal antibody according to claim 2, further comprising a human antibody light chain constant region, and a the hinge region including the antibody heavy chain variable region and a human antibody heavy chain constant region, wherein the human antibody heavy chain constant region includes a constant heavy region 1 (CH1), a constant heavy region 2 (CH2) and a constant heavy region 3 (CH3).

14. The daughter cell according to claim 8, wherein, the first variable region is an antibody light chain variable region having the amino acid sequence of SEQ ID NO: 11, and the second variable region is an antibody heavy chain variable region having the amino acid sequence of SEQ ID NO: 12.

15. The medicine according to claim 9, wherein, the first variable region is an antibody light chain variable region having the amino acid sequence of SEQ ID NO: 11, and the second variable region is an antibody heavy chain variable region having the amino acid sequence of SEQ ID NO: 12.

* * * * *